(12) United States Patent
Yamatani

(10) Patent No.: US 10,818,850 B2
(45) Date of Patent: Oct. 27, 2020

(54) ORGANIC ELECTROLUMINESCENCE DEVICE AND COMPOUND INCLUDING NITROGEN FOR ORGANIC ELECTROLUMINESCENCE DEVICE

(71) Applicant: Samsung Display Co., Ltd., Yongin-si, Gyeonggi-do (KR)

(72) Inventor: Akinori Yamatani, Yokohama (JP)

(73) Assignee: Samsung Display Co., Ltd., Yongin-si (KR)

( * ) Notice: Subject to any disclaimer, the term of this patent is extended or adjusted under 35 U.S.C. 154(b) by 226 days.

(21) Appl. No.: 16/129,666

(22) Filed: Sep. 12, 2018

(65) Prior Publication Data
US 2019/0198773 A1    Jun. 27, 2019

(30) Foreign Application Priority Data
Dec. 22, 2017   (KR) .................. 10-2017-0178632

(51) Int. Cl.
*H01L 51/50* (2006.01)
*H01L 51/00* (2006.01)
(Continued)

(52) U.S. Cl.
CPC ........ *H01L 51/0072* (2013.01); *C07D 401/14* (2013.01); *C07D 403/10* (2013.01);
(Continued)

(58) Field of Classification Search
None
See application file for complete search history.

(56) References Cited

U.S. PATENT DOCUMENTS

| 5,332,833 A | 7/1994 | Sekiya et al. |
| 6,265,426 B1 | 7/2001 | Alanine et al. |

(Continued)

FOREIGN PATENT DOCUMENTS

| CN | 101333438 B | 11/2011 |
| CN | 102709483 A | 10/2012 |

(Continued)

OTHER PUBLICATIONS

Leung et al., Novel Ambipolar Orthogonal Donor-Acceptor Host for Blue Organic Light Emitting Diodes; 2013; Organic Letters, 15(18), 4694-4697 (Year: 2013).*

(Continued)

*Primary Examiner* — Gregory D Clark
(74) *Attorney, Agent, or Firm* — Lewis Roca Rothgerber Christie LLP

(57) ABSTRACT

An organic electroluminescence device and a compound including nitrogen for an organic electroluminescence device are provided. The compound including nitrogen according to an embodiment of the present disclosure is represented by Formula 1. In Formula 1, "n" is 0 or 1, and $M_1$ and $M_2$ are each independently represented by Formula 2 or 3:

Formula 1

(Continued)

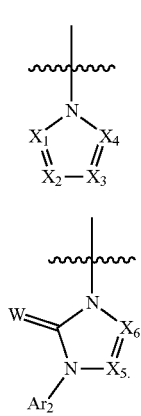

Formula 2

Formula 3

22 Claims, 2 Drawing Sheets

(51) Int. Cl.
| | |
|---|---|
| C07D 403/10 | (2006.01) |
| C07D 487/04 | (2006.01) |
| C07D 417/10 | (2006.01) |
| C07D 401/14 | (2006.01) |
| C07F 7/08 | (2006.01) |
| C07D 403/14 | (2006.01) |
| C07F 5/02 | (2006.01) |
| C07D 409/14 | (2006.01) |
| C07D 471/14 | (2006.01) |
| C07D 405/14 | (2006.01) |
| C07F 9/6558 | (2006.01) |
| C07D 413/10 | (2006.01) |

(52) U.S. Cl.
CPC ......... *C07D 403/14* (2013.01); *C07D 405/14* (2013.01); *C07D 409/14* (2013.01); *C07D 413/10* (2013.01); *C07D 417/10* (2013.01); *C07D 471/14* (2013.01); *C07D 487/04* (2013.01); *C07F 5/02* (2013.01); *C07F 7/0812* (2013.01); *C07F 9/65583* (2013.01); *H01L 51/0067* (2013.01); *H01L 51/0069* (2013.01); *H01L 51/0085* (2013.01); *H01L 51/5016* (2013.01); *H01L 51/5056* (2013.01); *H01L 51/5072* (2013.01); *H01L 51/5088* (2013.01); *H01L 51/5092* (2013.01); *H01L 51/5096* (2013.01)

(56) References Cited

U.S. PATENT DOCUMENTS

| | | | |
|---|---|---|---|
| 6,696,487 | B2 | 2/2004 | Gerusz et al. |
| 6,743,789 | B2 | 6/2004 | Masciadri et al. |
| 6,759,538 | B2 | 7/2004 | Singh et al. |
| 7,220,745 | B2 | 5/2007 | Singh et al. |
| 7,326,726 | B2 | 2/2008 | Chakravarty et al. |
| 7,714,099 | B2 | 5/2010 | Morishita et al. |
| 7,994,171 | B2 | 8/2011 | Yeung et al. |
| 8,017,635 | B2 | 9/2011 | Lyga et al. |
| 8,048,887 | B2 | 11/2011 | Yeung et al. |
| 9,359,389 | B2 | 6/2016 | Bittman et al. |
| 9,421,211 | B2 | 8/2016 | Aktas et al. |
| 2015/0243902 | A1 | 8/2015 | Wang et al. |
| 2016/0087227 | A1 | 3/2016 | Kim et al. |
| 2016/0318856 | A1 | 11/2016 | Aktas et al. |
| 2017/0162794 | A1 | 6/2017 | Ting et al. |
| 2017/0233354 | A1 | 8/2017 | Valmier et al. |
| 2018/0016243 | A1 | 1/2018 | Meyerhans et al. |

FOREIGN PATENT DOCUMENTS

| | | |
|---|---|---|
| DE | 10 2005 000 903 A1 | 7/2006 |
| EP | 0548680 A1 | 6/1993 |
| EP | 1 070 708 A1 | 1/2001 |
| EP | 1 178 039 A1 | 2/2002 |
| JP | 8-176148 A | 7/1996 |
| JP | 2005-225819 A | 8/2005 |
| JP | 2008-516008 A | 5/2008 |
| KR | 10-1256205 B1 | 4/2013 |
| KR | 10-2014-0125117 A | 10/2014 |
| KR | 10-2015-0037133 A | 4/2015 |
| WO | WO 02/40487 A2 | 5/2002 |
| WO | WO 03/040112 A1 | 5/2003 |
| WO | WO 2004/083189 A1 | 9/2004 |
| WO | WO 2006/130403 A1 | 12/2006 |
| WO | WO 2010/030592 A1 | 3/2010 |
| WO | WO 2010/098488 A1 | 9/2010 |
| WO | WO 2010/138820 A2 | 12/2010 |
| WO | WO 2011/056599 A2 | 5/2011 |
| WO | WO 2011/112191 A1 | 9/2011 |
| WO | WO 2015/038778 A1 | 3/2015 |
| WO | WO 2016/016370 A1 | 2/2016 |
| WO | WO 2016/116485 A1 | 7/2016 |
| WO | WO 2016/128541 A1 | 8/2016 |
| WO | WO 2016/174377 A1 | 11/2016 |

OTHER PUBLICATIONS

Extended European Search Report for corresponding European Application No. 18211134.4, dated Apr. 5, 2019, 9 pages.
Database Registry [Online]; Chemical Abstracts Service, Columbus, Ohio, US; XP002790062, Database accession No. 1027938-27-7 *compound cas rn: 1027938-27-7*, Jun. 13, 2008, 1 pages.
Database Registry [Online]; Chemical Abstracts Service, Columbus, Ohio, US; XP002790063, Database accession No. 460326-53-8 *compound cas rn: 460326-53-8*, Oct. 10, 2002, 1 pages.

\* cited by examiner

ORGANIC ELECTROLUMINESCENCE DEVICE AND COMPOUND INCLUDING NITROGEN FOR ORGANIC ELECTROLUMINESCENCE DEVICE

CROSS-REFERENCE TO RELATED APPLICATION

This application claims priority to and the benefit of Korean Patent Application No. 10-2017-0178632, filed on Dec. 22, 2017, the entire content of which is hereby incorporated by reference.

BACKGROUND

One or more embodiments of the present disclosure herein relate to an organic electroluminescence device and a compound including nitrogen for an organic electroluminescence device.

Recently, the development of an organic electroluminescence device as an image display device is being actively conducted. Different from a liquid crystal display device, an organic electroluminescence display device is a self-luminescent display device in which holes and electrons injected from a first electrode and a second electrode recombine in an emission layer, and a light emission material including an organic compound in the emission layer emits light to attain display (e.g., realize the display of images).

In the application of an organic electroluminescence device to a display device, the decrease of a driving voltage, and the increase of emission efficiency and life are desired, and the development of a material for stably accomplishing the improved characteristics for an organic electroluminescence device is continuously desired.

SUMMARY

One or more embodiments of the present disclosure are directed toward an organic electroluminescence device and a compound including nitrogen for an organic electroluminescence device.

An embodiment of the present disclosure provides an organic electroluminescence device including a first electrode, a hole transport region on the first electrode, an emission layer on the hole transport region, an electron transport region on the emission layer, and a second electrode on the electron transport region, wherein the emission layer includes a compound including nitrogen, represented by the following Formula 1:

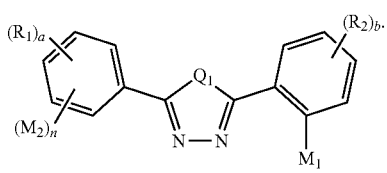

Formula 1

In Formula 1, $Q_1$ is $NAr_1$, O or S, $Ar_1$ is a hydrogen atom, a deuterium atom, a substituted or unsubstituted aryl group having 6 to 30 carbon atoms for forming a ring, or a substituted or unsubstituted heteroaryl group having 2 to 30 carbon atoms for forming a ring, $R_1$ and $R_2$ are each independently a hydrogen atom, a deuterium atom, a halogen atom, a substituted or unsubstituted amino group, a substituted or unsubstituted silyl group, a substituted or unsubstituted boryl group, a substituted or unsubstituted alkyl group having 1 to 10 carbon atoms, a substituted or unsubstituted aralkyl group having 6 to 30 carbon atoms, a substituted or unsubstituted haloalkyl group having 1 to 10 carbon atoms, a substituted or unsubstituted aryloxy group having 6 to 30 carbon atoms, a substituted or unsubstituted arylthio group having 6 to 30 carbon atoms, a substituted or unsubstituted phosphine oxy group, a substituted or unsubstituted phosphine sulfide group, a substituted or unsubstituted aryl group having 6 to 30 carbon atoms for forming a ring, or a substituted or unsubstituted heteroaryl group having 2 to 30 carbon atoms for forming a ring, where adjacent $R_1$ and $R_2$ may each independently be combined with an adjacent group to form a ring, "a" and "b" are each independently an integer of 0 to 4, "n" is 0 or 1, and $M_1$ and $M_2$ are each independently represented by the following Formulae 2 or 3:

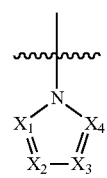

Formula 2

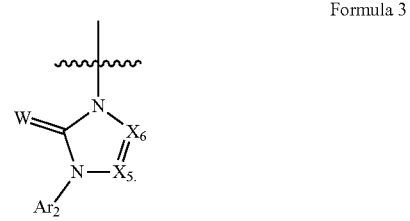

Formula 3

In Formulae 2 and 3, $X_1$ to $X_6$ are each independently $CR_3$ or N, at least one of $X_1$ to $X_4$ is N, $R_3$ is a hydrogen atom, a deuterium atom, a substituted or unsubstituted alkyl group having 1 to 10 carbon atoms, a substituted or unsubstituted aryl group having 6 to 30 carbon atoms for forming a ring, or a substituted or unsubstituted heteroaryl group having 2 to 30 carbon atoms for forming a ring, and one or more of $R_3$ may be combined with an adjacent group to form a ring, W is O, $NAr_3$, or $CAr_4Ar_5$, $Ar_2$ to $Ar_5$ are each independently a hydrogen atom, a deuterium atom, a substituted or unsubstituted alkyl group having 1 to 10 carbon atoms, a substituted or unsubstituted aralkyl group, a substituted or unsubstituted aryl group having 6 to 30 carbon atoms for forming a ring, or a substituted or unsubstituted heteroaryl group having 2 to 30 carbon atoms for forming a ring, and $Ar_2$ to $Ar_5$ may each independently be combined with an adjacent group to form a ring.

In an embodiment, Formula 2 may be represented by one of the following Formulae 2-1 to 2-3:

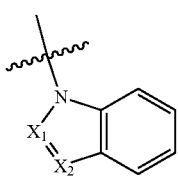

Formula 2-1

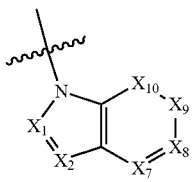

Formula 2-2

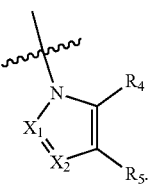

Formula 2-3

In Formulae 2-1 to 2-3, $X_1$ and $X_2$ are each independently $CR_3$ or N, where at least one of $X_1$ or $X_2$ is N, $X_7$ to $X_{10}$ are each independently $CR_6$ or N, where at least one of $X_7$ to $X_{10}$ is N, and $R_3$ to $R_6$ are each independently a hydrogen atom, a substituted or unsubstituted aryl group having 6 to 30 carbon atoms for forming a ring, or a substituted or unsubstituted heteroaryl group having 2 to 30 carbon atoms for forming a ring.

In an embodiment, Formula 3 may be represented by one of the following Formulae 3-1 to 3-4:

Formula 3-1

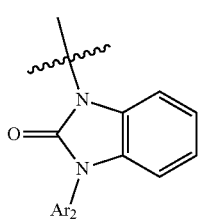

Formula 3-2

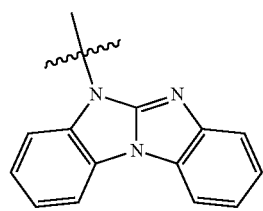

Formula 3-3

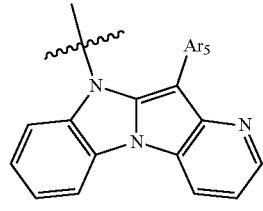

Formula 3-4

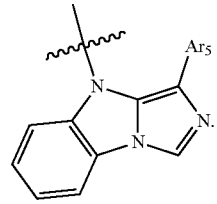

In Formulae 3-1, 3-3 and 3-4, $Ar_2$ and $Ar_5$ are each independently a substituted or unsubstituted aryl group having 6 to 30 carbon atoms for forming a ring, or a substituted or unsubstituted heteroaryl group having 2 to 30 carbon atoms for forming a ring.

In an embodiment, $Q_1$ may be $NAr_1$, and $Ar_1$ may be a substituted or unsubstituted phenyl group.

In an embodiment, Formula 1 may be represented by the following Formulae 1-1 or 1-2:

Formula 1-1

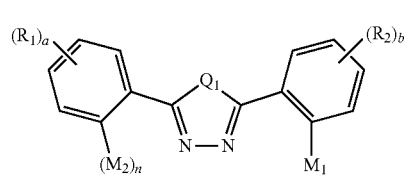

Formula 1-2

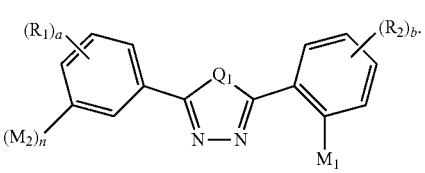

In Formulae 1-1 and 1-2, $Q_1$, $R_1$, $R_2$, $M_1$, $M_2$, "n", "a" and "b" are the same as defined above.

In an embodiment, "a" may be 0.

In an embodiment, Formula 1 may be represented by the following Formula 1-3:

Formula 1-3

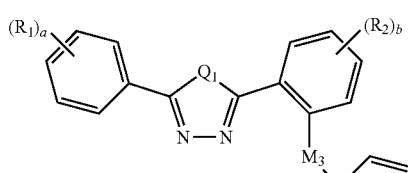

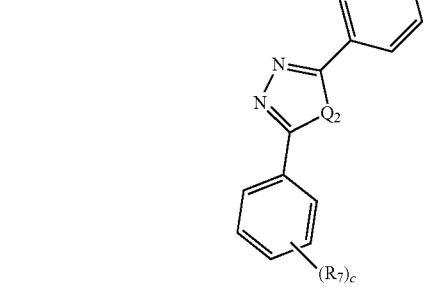

In Formula 1-3, $Q_1$, $R_1$, $R_2$, "a" and "b" are the same as defined in above, definition of $Q_2$ is the same as the definition of $Q_1$, $Q_1$ and $Q_2$ may be the same or different, $R_7$ is a hydrogen atom, a deuterium atom, a substituted or unsubstituted alkyl group having 1 to 10 carbon atoms, a substituted or unsubstituted aryl group having 6 to 30 carbon atoms for forming a ring, or a substituted or unsubstituted heteroaryl group having 2 to 30 carbon atoms for forming a ring, "c" is an integer of 0 to 5, and $M_3$ is represented by the following Formula 4:

Formula 4

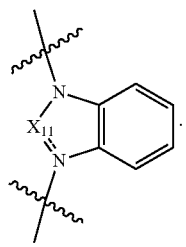

In Formula 4, $X_{11}$ is C=O, or $CR_8$, and $R_8$ is a hydrogen atom, a deuterium atom, a substituted or unsubstituted alkyl group having 1 to 10 carbon atoms, a substituted or unsubstituted aryl group having 6 to 30 carbon atoms for forming a ring, or a substituted or unsubstituted heteroaryl group having 2 to 30 carbon atoms for forming a ring.

In an embodiment, "b" may be 0 or 1, and if "b" is 1, $R_2$ may be the same as $M_1$.

In an embodiment, the compound including nitrogen, represented by Formula 1 may have the lowest triplet energy level of about 3.0 eV or more.

In an embodiment, the emission layer may include a host and a dopant, and the host may include the compound including nitrogen, represented by Formula 1 above.

In an embodiment, the dopant may be a phosphorescence dopant.

An embodiment of the present disclosure provides a compound including nitrogen, represented by Formula 1.

BRIEF DESCRIPTION OF THE FIGURES

The accompanying drawings are included to provide a further understanding of the present disclosure, and are incorporated in and constitute a part of this specification. The drawings illustrate example embodiments of the present disclosure and, together with the description, serve to explain principles of the present disclosure. In the drawings.

DETAILED DESCRIPTION

Figure 1:
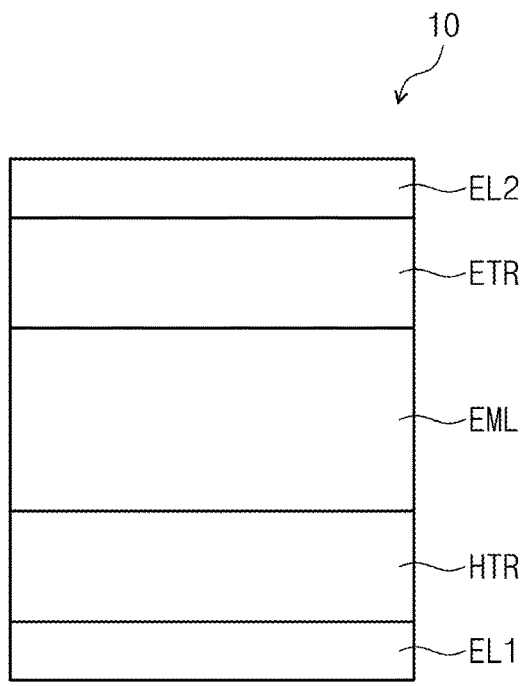
FIG. 1 is a cross-sectional view schematically illustrating an organic electroluminescence device according to an embodiment of the present disclosure.

The above objects, other objects, features and advantages of the present disclosure will be easily understood from example embodiments with reference to the accompanying drawings. The present disclosure may, however, be embodied in different forms and should not be construed as limited to the embodiments set forth herein. Rather, example embodiments are provided so that the contents disclosed herein become thorough and complete, and the spirit of the present disclosure is sufficiently understood for a person skilled in the art.

Like reference numerals refer to like elements for explaining each drawing. In the drawings, the sizes of elements may be enlarged for clarity of the present disclosure. It will be understood that, although the terms first, second, etc. may be used herein to describe various elements, these elements should not be limited by these terms. These terms are only used to distinguish one element from another element. For example, a first element discussed below could be termed a second element, and similarly, a second element could be termed a first element. As used herein, the singular forms are intended to include the plural forms as well, unless the context clearly indicates otherwise.

It will be further understood that the terms "comprises" or "comprising," when used in this specification, specify the presence of stated features, numerals, steps, operations, elements, parts, or a combination thereof, but do not preclude the presence or addition of one or more other features, numerals, steps, operations, elements, parts, or a combination thereof. It will also be understood that when a layer, a film, a region, a plate, etc. is referred to as being "on" another part, it can be "directly on" the other part, or intervening parts may also be present. Additionally, when a layer, a film, a region, a plate, etc. is referred to as being "under" another part, it can be "directly under" the other part, or intervening parts may also be present.

Expressions such as "at least one of," "one of," and "selected from," when preceding a list of elements, modify the entire list of elements and do not modify the individual elements of the list. Further, the use of "may" when describing embodiments of the present invention refers to "one or more embodiments of the present invention."

First, organic electroluminescence devices according to example embodiments of the present disclosure will be explained referring to FIG. 1 to FIG. 3.

FIG. 1 is a cross-sectional view schematically illustrating an organic electroluminescence device according to an embodiment of the present disclosure. FIG. 2 is a cross-sectional view schematically illustrating an organic electroluminescence device according to an embodiment of the present disclosure. FIG. 3 is a cross-sectional view schematically illustrating an organic electroluminescence device according to an embodiment of the present disclosure.

Figure 2:
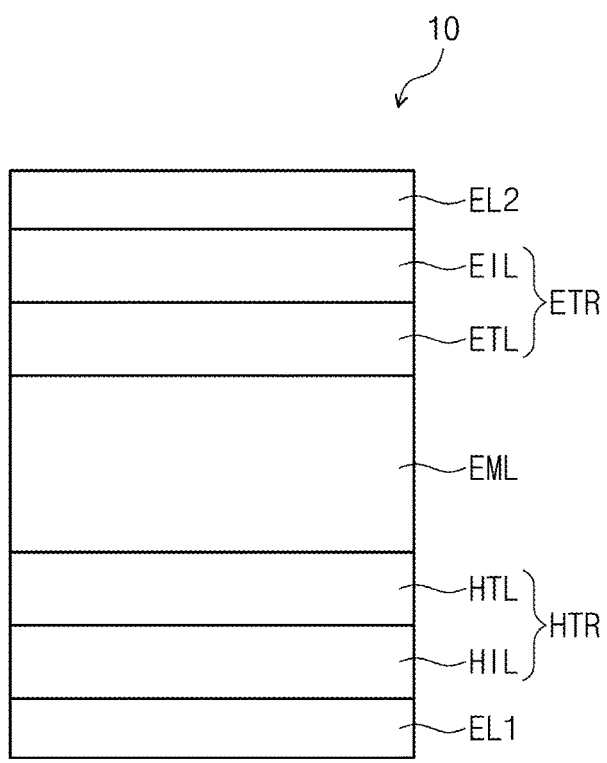
FIG. 2 is a cross-sectional view schematically illustrating an organic electroluminescence device according to an embodiment of the present disclosure.
Figure 3:
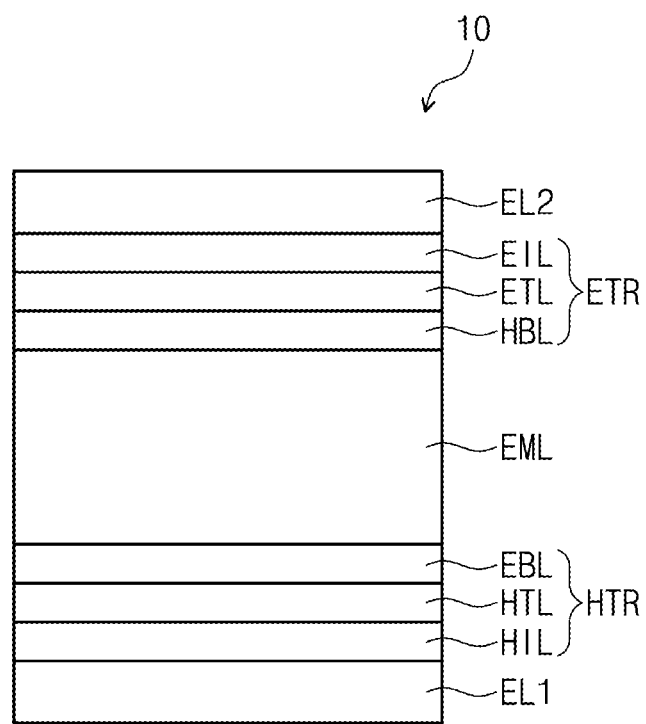
FIG. 3 is a cross-sectional view schematically illustrating an organic electroluminescence device according to an embodiment of the present disclosure.

Referring to FIG. 1 to FIG. 3, organic electroluminescence devices according to example embodiments of the present disclosure may include a first electrode EL1, a hole transport region HTR, an emission layer EML, an electron transport region ETR and a second electrode EL2.

The emission layer EML may include a compound including nitrogen according to an embodiment of the present disclosure. However, an embodiment of the present disclosure is not limited thereto. At least one layer among one or more organic layers disposed (e.g., positioned) between the first electrode EL1 and the second electrode EL2 may include the compound including nitrogen according to an embodiment of the present disclosure. For example, the hole transport region HTR may include the compound including nitrogen according to an embodiment of the present disclosure.

Hereinafter, the compound including nitrogen according to an embodiment of the present disclosure will be explained in more detail and then, each layer of an organic electroluminescence device 10 will be explained.

The compound including nitrogen according to an embodiment of the present disclosure may be represented by the following Formula 1:

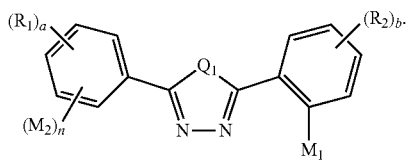

Formula 1

In Formula 1, $Q_1$ may be $NAr_1$, O or S, $Ar_1$ may be a hydrogen atom, a deuterium atom, a substituted or unsubstituted aryl group having 6 to 30 carbon atoms for forming a ring, or a substituted or unsubstituted heteroaryl group having 2 to 30 carbon atoms for forming a ring, $R_1$ and $R_2$ may each independently be a hydrogen atom, a deuterium atom, a halogen atom, a substituted or unsubstituted amino group, a substituted or unsubstituted silyl group, a substituted or unsubstituted boryl group, a substituted or unsubstituted alkyl group having 1 to 10 carbon atoms, a substituted or unsubstituted aralkyl group having 6 to 30 carbon atoms, a substituted or unsubstituted haloalkyl group having 1 to 10 carbon atoms, a substituted or unsubstituted aryloxy group having 6 to 30 carbon atoms, a substituted or unsubstituted arylthio group having 6 to 30 carbon atoms, a substituted or unsubstituted phosphine oxy group (e.g., phosphine oxide group), a substituted or unsubstituted phosphine sulfide group, a substituted or unsubstituted aryl group having 6 to 30 carbon atoms for forming a ring, or a substituted or unsubstituted heteroaryl group having 2 to 30 carbon atoms for forming a ring, where $R_1$ and $R_2$ may each independently be combined with an adjacent group to form a ring, "a" and "b" may each independently be an integer of 0 to 4, "n" is 0 or 1, and $M_1$ and $M_2$ may each independently be represented by the following Formula 2 or 3:

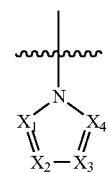

Formula 2

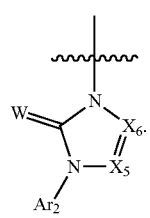

Formula 3

In Formula 2, $X_1$ to $X_4$ may each independently be $CR_3$ or N, where at least one of $X_1$ to $X_4$ may be N, $R_3$ may be a hydrogen atom, a deuterium atom, a substituted or unsubstituted alkyl group having 1 to 10 carbon atoms, a substituted or unsubstituted aryl group having 6 to 30 carbon atoms for forming a ring, or a substituted or unsubstituted heteroaryl group having 2 to 30 carbon atoms for forming a ring, and $R_3$ may be combined with an adjacent group to form a ring.

In Formula 3, $X_5$ and $X_6$ may each independently be $CR_3$ or N, $R_3$ may be a hydrogen atom, a deuterium atom, a substituted or unsubstituted alkyl group having 1 to 10 carbon atoms, a substituted or unsubstituted aryl group having 6 to 30 carbon atoms for forming a ring, or a substituted or unsubstituted heteroaryl group having 2 to 30 carbon atoms for forming a ring, and $R_3$ may be combined with an adjacent group to form a ring, W may be O, $NAr_3$, or $CAr_4Ar_5$, $Ar_2$ to $Ar_5$ may each independently be a hydrogen atom, a deuterium atom, a substituted or unsubstituted alkyl group having 1 to 10 carbon atoms, a substituted or unsubstituted aralkyl group, a substituted or unsubstituted aryl group having 6 to 30 carbon atoms for forming a ring, or a substituted or unsubstituted heteroaryl group having 2 to 30 carbon atoms for forming a ring, and $Ar_2$ to $Ar_5$ may each independently be combined with an adjacent group to form a ring.

In the present disclosure,

may refer to a part to be connected (e.g., a binding site).

In the present disclosure, "substituted or unsubstituted" may refer to a group that is unsubstituted or that is substituted with at least one substituent selected from a deuterium atom, a halogen group, a cyano group, a nitro group, an amino group, a silyl group, an oxy group, a thio group, a sulfinyl group, a sulfonyl group, a carbonyl group, a boron group, an aryl amine group, a phosphine oxide group, a phosphine sulfide group, an alkyl group, an alkenyl group, an aryl group, and a heterocyclic group. In addition, each of the substituent illustrated above may be substituted or unsubstituted. For example, a biphenyl group may be described as an aryl group, or a phenyl group substituted with a phenyl group.

In the present disclosure, the terms "forming a ring via the combination with an adjacent group" may refer to forming a substituted or unsubstituted hydrocarbon ring, or a substituted or unsubstituted heterocycle via the combination of one group with an adjacent group. The hydrocarbon ring may include an aliphatic hydrocarbon ring and an aromatic hydrocarbon ring. The heterocycle may include an aliphatic heterocycle and an aromatic heterocycle. The hydrocarbon ring and the heterocycle may each independently be monocyclic or polycyclic. In addition, the ring formed via the combination with an adjacent group may be combined with another ring to form a spiro structure.

In the present disclosure, the terms "an adjacent group" may refer to a pair of substituent groups where the first substituent is connected to an atom which is directly connected to another atom substituted with the second substituent, a pair of substituent groups connected to the same atom, or a pair of substituent groups where the first substituent is sterically positioned at the nearest position to the second substituent. For example, in 1,2-dimethylbenzene, two methyl groups may be interpreted as "adjacent groups" to each other, and in 1,1-diethylcyclopentene, two ethyl groups may be interpreted as "adjacent groups" to each other.

In the present disclosure, the halogen atom may include a fluorine atom, a chlorine atom, a bromine atom and/or an iodine atom, but is not limited thereto.

In the present disclosure, the alkyl group may be a linear, branched or cyclic group. The carbon number of the alkyl group may be from 1 to 30, from 1 to 20, from 1 to 10, or from 1 to 4. The alkyl group may include methyl, ethyl, n-propyl, isopropyl, n-butyl, s-butyl, t-butyl, i-butyl, 2-ethylbutyl, 3,3-dimethylbutyl, n-pentyl, i-pentyl, neopentyl, t-pentyl, cyclopentyl, 1-methylpentyl, 3-methylpentyl, 2-ethylpentyl, 4-methyl-2-pentyl, n-hexyl, 1-methylhexyl, 2-ethylhexyl, 2-butylhexyl, cyclohexyl, 4-methylcyclohexyl, 4-t-butylcyclohexyl, n-heptyl, 1-methylheptyl, 2,2-dimethylheptyl, 2-ethylheptyl, 2-butylheptyl, n-octyl, t-octyl, 2-ethyloctyl, 2-butyloctyl, 2-hexyloctyl, 3,7-dimethyloctyl, cyclooctyl, n-nonyl, n-decyl, adamantyl, 2-ethyldecyl, 2-butyldecyl, 2-hexyldecyl, 2-octyldecyl, n-undecyl, n-dodecyl, 2-ethyldodecyl, 2-butyldodecyl, 2-hexyldocecyl, 2-octyldodecyl, n-tridecyl, n-tetradecyl, c-pentadecyl, n-hexadecyl, 2-ethylhexadecyl, 2-butylhexadecyl, 2-hexylhexadecyl, 2-octylhexadecyl, n-heptadecyl, n-octadecyl, n-nonadecyl, n-eicosyl, 2-ethyleicosyl, 2-butyleicosyl, 2-hexyleicosyl, 2-octyleicosyl, n-henicosyl, n-docosyl, n-tricosyl, n-tetracosyl, n-pentacosyl, n-hexacosyl, n-heptacosyl, n-octacosyl, n-nonacosyl, n-triacontyl, etc., without limitation.

In the present disclosure, the aryl group may refer to a functional group or substituent derived from an aromatic hydrocarbon ring. The aryl group may be a monocyclic aryl group or a polycyclic aryl group. The carbon number for forming a ring in the aryl group may be, 6 to 30, 6 to 20, or 6 to 15. Examples of the aryl group may include phenyl, naphthyl, fluorenyl, anthracenyl, phenanthryl, biphenyl, terphenyl, quaterphenyl, quinqphenyl, sexiphenyl, biphenylenyl, triphenylenyl, pyrenyl, benzofluoranthenyl, chrysenyl, etc., without limitation.

In the present disclosure, the fluorenyl group may be substituted, and two substituents may be combined with each other to form a spiro structure. Non-limiting examples of the substituted fluorenyl group are shown below. However, embodiments of the present disclosure are not limited thereto:

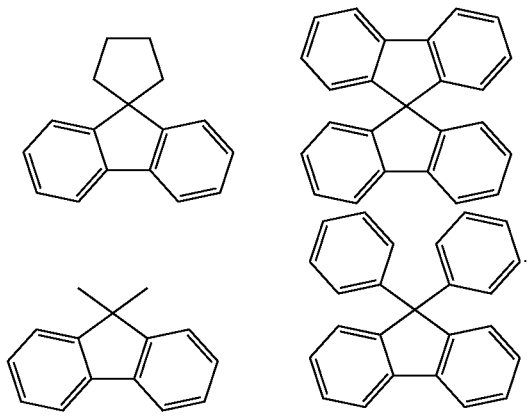

In the present disclosure, the alkyl group in haloalkyl, alkoxy, aralkyl and alkylthio groups may be the same as the above-described alkyl group.

In the present disclosure, the aryl group in aryloxy, aralkyl and arylthio groups may be the same as the above-described aryl group.

In the present disclosure, the heteroaryl may be a heteroaryl group (e.g., a cyclic aromatic group) including at least one of O, N, P, Si or S as a heteroatom. If the heteroaryl group includes two heteroatoms, the two heteroatoms may be the same or different. The carbon number for forming a ring of the heteroaryl group may be 2 to 30, or 2 to 20. The heteroaryl group may be monocyclic heteroaryl or polycyclic heteroaryl. Examples of the polycyclic heteroaryl may have dicyclic or tricyclic structure. Examples of the heteroaryl group may include thiophene, furan, pyrrole, imidazole, thiazole, oxazole, oxadiazole, triazole, pyridine, bipyridine, pyrimidine, triazine, triazole, acridine, pyridazine, pyrazine, quinoline, quinazoline, quinoxaline, phenoxazine, phthalazine, pyrido pyrimidine, pyrido pyrazine, pyrazino pyrazine, isoquinoline, indole, carbazole, N-arylcarbazole, N-heteroarylcarbazole, N-alkylcarbazole, benzoxazole, benzoimidazole, benzothiazole, benzocarbazole, benzothiophene, dibenzothiophene, thienothiophene, benzofuran, phenanthroline, thiazole, isooxazole, oxadiazole, thiadiazole, phenothiazine, dibenzosilole, dibenzofuran, etc., without limitation.

In the present disclosure, the silyl group may include an alkyl silyl group and an aryl silyl group, without limitation. Examples of the silyl group may include trimethylsilyl, triethylsilyl, t-butyldimethylsilyl, vinyldimethylsilyl, propyldimethylsilyl, triphenylsilyl, diphenylsilyl, phenylsilyl, etc. However, embodiments of the present disclosure are not limited thereto.

In the present disclosure, the boron group (boryl group) may include an alkyl boron group and an aryl boron group, without limitation. Examples of the boron group include trimethylboron, triethylboron, t-butyldimethylboron, triphenylboron, diphenylboron, phenylboron, etc., without limitation.

In the present disclosure, the alkenyl group may have a linear chain or a branched chain. The carbon number of the alkenyl group is not specifically limited and may be 2 to 30, 2 to 20, or 2 to 10. Examples of the alkenyl group include vinyl, 1-butenyl, 1-pentenyl, 1,3-butadienyl aryl, styrenyl, styrylvinyl, etc., without limitation.

In the present disclosure, the carbon number of the amino group is not specifically limited, but may be 1 to 30. The amino group may include an alkyl amino group and an aryl amino group, without limitation. Examples of the amino group include a methylamino group, a dimethylamino group, a phenylamine group, a diphenylamino group, a naphthylamino group, a 9-methyl-anthracenylamino group, a triphenylamino group, etc., without limitation.

In the present disclosure, the phosphine oxy group (e.g., phosphine oxide group) may be, for example, substituted with at least one of the alkyl group or the aryl group.

In the present disclosure, the phosphine sulfide group may be, for example, substituted with at least one of the alkyl group or the aryl group.

In Formula 1, if "a" is 1, $R_1$ may not be a hydrogen atom, and if "b" is 1, $R_2$ may not be a hydrogen atom. If "a" is 2 or more, a plurality of $R_1$ groups may be the same or different, and if "b" is 2 or more, a plurality of $R_2$ groups may be the same or different.

In Formula 1, if $R_1$ groups are plural (e.g., if two or more $R_1$ groups are present), adjacent two $R_1$ groups may be combined with each other to form a ring, for example, a heterocycle.

In Formulae 2 and 3, if $R_3$ groups are plural, adjacent two $R_3$ groups may be combined with each other to form a ring.

In Formula 2, the number of N in $X_1$ to $X_4$ may be 1, 2 or 3 (e.g., 1, 2, or 3 of $X_1$ to $X_4$ may be nitrogen).

Formula 2 may be represented by one of the following Formulae 2-1 to 2-3:

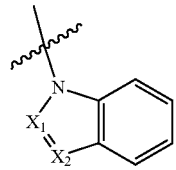

Formula 2-1

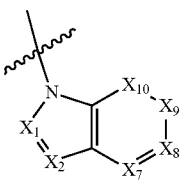

Formula 2-2

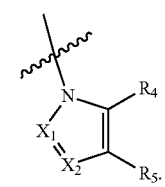

Formula 2-3

In Formula 2-1, $X_1$ and $X_2$ may each independently be $CR_3$ or N, and at least one of $X_1$ or $X_2$ my be N, and $R_3$ may be a hydrogen atom, a substituted or unsubstituted aryl group having 6 to 30 carbon atoms for forming a ring, or a substituted or unsubstituted heteroaryl group having 2 to 30 carbon atoms for forming a ring.

In Formula 2-1, $R_3$ may be a hydrogen atom, a substituted or unsubstituted phenyl group, or a substituted or unsubstituted heteroaryl group including nitrogen. The heteroaryl group including nitrogen may be, for example, a substituted or unsubstituted pyridine group, or a substituted or unsubstituted pyrimidine group, without limitation.

In Formula 2-2, $X_1$ and $X_2$ may each independently be $CR_3$ or N, and at least one of $X_1$ or $X_2$ may be N, $X_7$ to $X_{10}$ may each independently be $CR_6$ or N, and at least one of $X_7$ to $X_{10}$ may be N, and $R_3$ and $R_6$ may each independently be a hydrogen atom, a substituted or unsubstituted aryl group having 6 to 30 carbon atoms for forming a ring, or a substituted or unsubstituted heteroaryl group having 2 to 30 carbon atoms for forming a ring.

In Formula 2-3, $X_1$ and $X_2$ may each independently be $CR_3$ or N, and at least one of $X_1$ or $X_2$ may be N, and $R_3$ to $R_5$ may each independently be a hydrogen atom, a substituted or unsubstituted aryl group having 6 to 30 carbon atoms for forming a ring, or a substituted or unsubstituted heteroaryl group having 2 to 30 carbon atoms for forming a ring.

Formula 2-1 may be represented by one of the following Formulae 2-1-1 to 2-1-3:

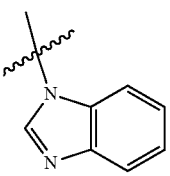

Formula 2-1-1

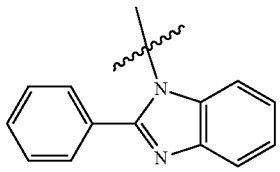

Formula 2-1-2

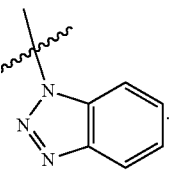

Formula 2-1-3

Formula 2-2 may be represented by, for example, the following Formula 2-2-1:

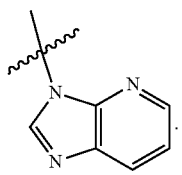

Formula 2-2-1

Formula 2-3 may be represented by one of the following Formulae 2-3-1 to 2-3-4:

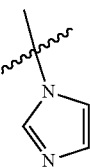

Formula 2-3-1

Formula 2-3-2

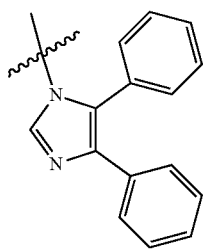

Formula 2-3-3

-continued

Formula 2-3-4

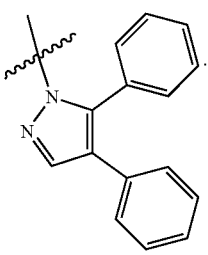

In Formula 3, W may be O. However, an embodiment of the present disclosure is not limited thereto, and W may be NAr₃, and Ar₃ may be combined with Ar₂ to form a ring. In another embodiment, in Formula 2, W may be CAr₄Ar₅, and one of Ar₄ and Ar₅ may be combined with Ar₂ to form a ring.

Formula 3 may be represented by one of the following Formulae 3-1 to 3-4:

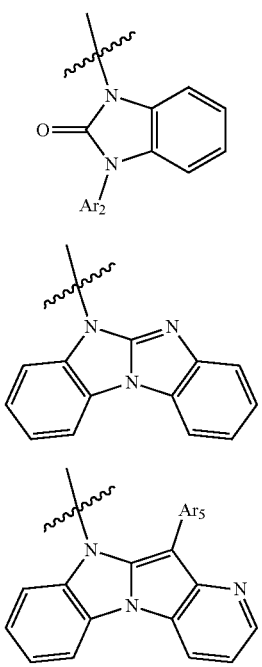

Formula 3-1

Formula 3-2

Formula 3-3

Formula 3-4

In Formula 3-1, Ar₂ may be a substituted or unsubstituted aryl group having 6 to 30 carbon atoms for forming a ring, or a substituted or unsubstituted heteroaryl group having 2 to 30 carbon atoms for forming a ring. In Formula 3-1, Ar₂ may be, for example, a substituted or unsubstituted phenyl group.

In Formula 3-3, Ar₅ may be a substituted or unsubstituted aryl group having 6 to 30 carbon atoms for forming a ring, or a substituted or unsubstituted heteroaryl group having 2 to 30 carbon atoms for forming a ring. In Formula 3-3, Ar₅ may be, for example, a substituted or unsubstituted phenyl group.

In Formula 3-4, Ar₅ may be a substituted or unsubstituted aryl group having 6 to 30 carbon atoms for forming a ring, or a substituted or unsubstituted heteroaryl group having 2 to 30 carbon atoms for forming a ring. In Formula 3-4, Ar₅ may be, for example, a substituted or unsubstituted phenyl group.

In Formula 1, $Q_1$ may be $NAr_1$, and $Ar_1$ may be a substituted or unsubstituted phenyl group. For example, $Q_1$ may be $NAr_1$, and $Ar_1$ may be a phenyl group which is substituted with a silyl group or unsubstituted. For example, $Q_1$ may be $NAr_1$, and $Ar_1$ may be a phenyl group which is substituted with a triphenylsilyl group or unsubstituted. However, embodiments of the present disclosure are not limited thereto. In Formula 1, $Q_1$ may be O or S.

Formula 1 may be represented by, for example, the following Formula 1-1 or 1-2:

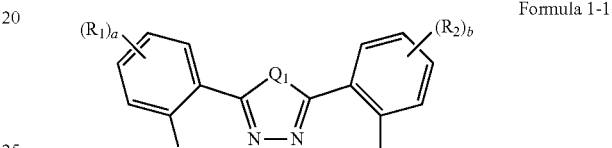

Formula 1-1

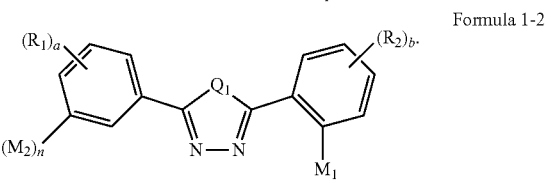

Formula 1-2

In Formulae 1-1 and 1-2, $Q_1$, $R_1$, $R_2$, $M_1$, $M_2$, "n", "a" and "b" are the same as defined above.

In Formulae 1-1 and 1-2, if "n" is 1, $M_1$ and $M_2$ may be the same. However, embodiments of the present disclosure are not limited thereto.

For example, "n" may be 1, and $M_1$ and $M_2$ may be represented by Formula 2-2-1 above. In another embodiment, "n" may be 1, and $M_1$ and $M_2$ may be represented by Formula 2-2-2 above. "n" may be 1, and $M_1$ and $M_2$ may be represented by Formula 3-2 above.

Formula 1 may be represented by, for example, the following Formula 1-3:

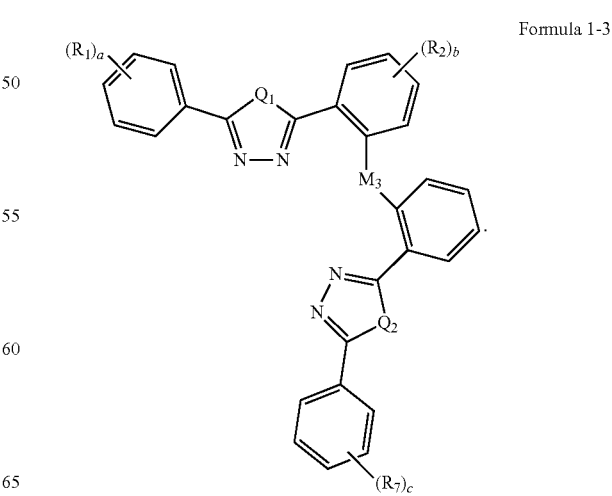

Formula 1-3

In Formula 1-3, $Q_1$, $R_1$, $R_2$, "a" and "b" are the same as defined above, definition of $Q_2$ is the same as the definition of $Q_1$, $Q_1$ and $Q_2$ may be the same or different, $R_7$ may be a hydrogen atom, a deuterium atom, a substituted or unsubstituted alkyl group having 1 to 10 carbon atoms, a substituted or unsubstituted aryl group having 6 to 30 carbon atoms for forming a ring, or a substituted or unsubstituted heteroaryl group having 2 to 30 carbon atoms for forming a ring, and "c" is an integer of 0 to 5.

In Formula 1-3, if "c" is 1, $R_7$ may not be a hydrogen atom, and if "c" is 2 or more, a plurality of $R_7$ groups may be the same or different. "c" may be 0, but embodiments of the present disclosure are not limited thereto.

In Formula 1-3, $M_3$ may be represented by the following Formula 4:

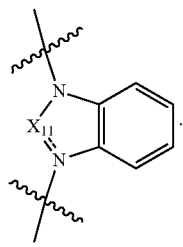

Formula 4

In Formula 4, $X_{11}$ may be C=O, or $CR_8$, and $R_8$ may be a hydrogen atom, a deuterium atom, a substituted or unsubstituted alkyl group having 1 to 10 carbon atoms, a substituted or unsubstituted aryl group having 6 to 30 carbon atoms for forming a ring, or a substituted or unsubstituted heteroaryl group having 2 to 30 carbon atoms for forming a ring.

In Formula 4, if $X_{11}$ is C=O, $X_{11}$ and two N atoms are connected via single bonds, and if $X_{11}$ is $CR_8$, one of two N atoms is connected with $CR_8$ via a double bond.

In Formula 4, $R_8$ may be a hydrogen atom, or a substituted or unsubstituted phenyl group.

In Formula 1, "a" may be 0. For example, a benzene ring which may be substituted with $M_2$ may be monosubstituted with $M_2$ or unsubstituted. "a" may be 1 or more, and $R_1$ may be a substituent other than a hydrogen atom. However, embodiments of the present disclosure are not limited thereto. For example, $R_1$ may be an arylamine group, an arylsilyl group, a phosphine oxy group, a phosphine sulfide group, an arylboryl group, a halogen atom, and/or a haloalkyl group, without limitation.

Formula 1 may be represented by the following Formula 1-4:

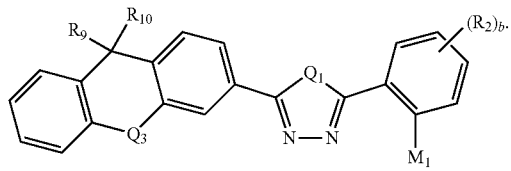

Formula 1-4

In Formula 1-4, $Q_3$ may be O, S, or $NR_{11}$, $R_9$ to $R_{11}$ may each independently be a hydrogen atom, a deuterium atom, a substituted or unsubstituted alkyl group having 1 to 10 carbon atoms, or a substituted or unsubstituted aryl group having 6 to 30 carbon atoms for forming a ring, and $Q_1$, $M_1$, $R_2$ and "b" are the same as described above.

In Formula 1, "b" may be 0. "b" may be 1, but an embodiment of the present disclosure is not limited thereto. If "b" is 1, $R_2$ and $M_1$ may be the same. For example, "b" may be 1, and $R_2$ and $M_1$ may be represented by Formula 2-2-1. In another embodiment, "b" may be 1, and $R_2$ and $M_1$ may be represented by Formula 2-2-2.

In another embodiment, "b" may be 1 or more, and $R_2$ may be a substituent other than a hydrogen atom. For example, $R_1$ may be an arylamine group, an arylsilyl group, a phosphine oxy group, a phosphine sulfide group, an arylboryl group, a halogen atom, and/or a haloalkyl group, without limitation.

The compound including nitrogen, represented by Formula 1 may be at least one selected from the compounds represented in Compound Group 1. However, an embodiment of the present disclosure is not limited thereto.

Compound Group 1

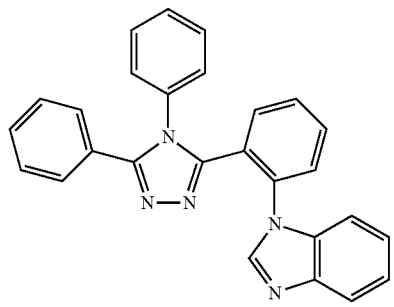

1

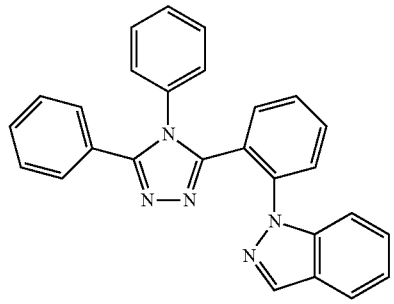

2

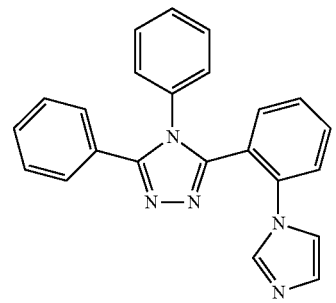

3

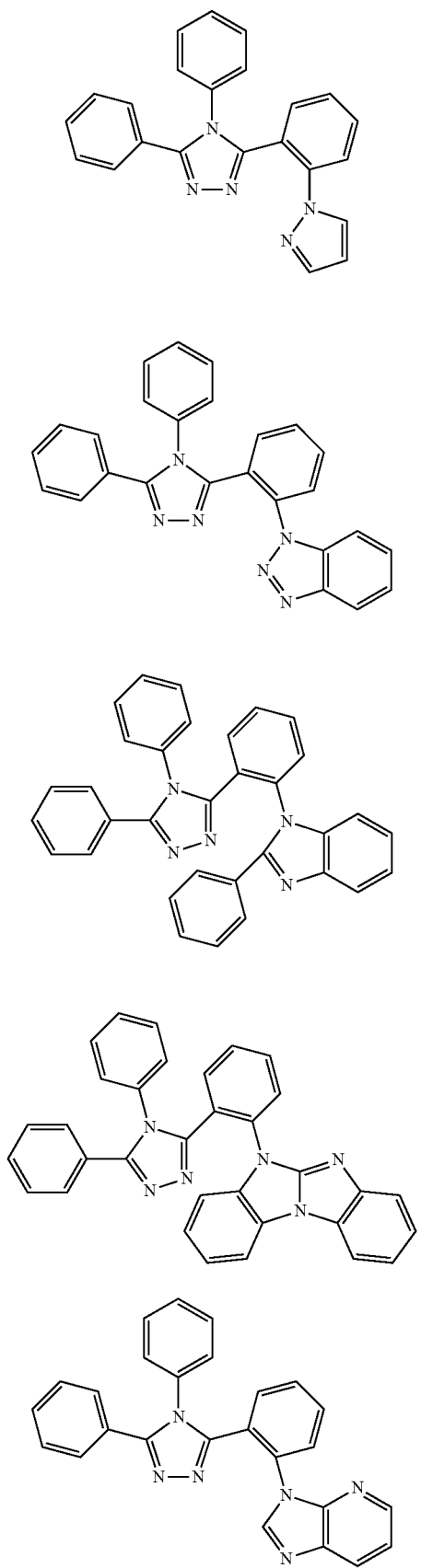
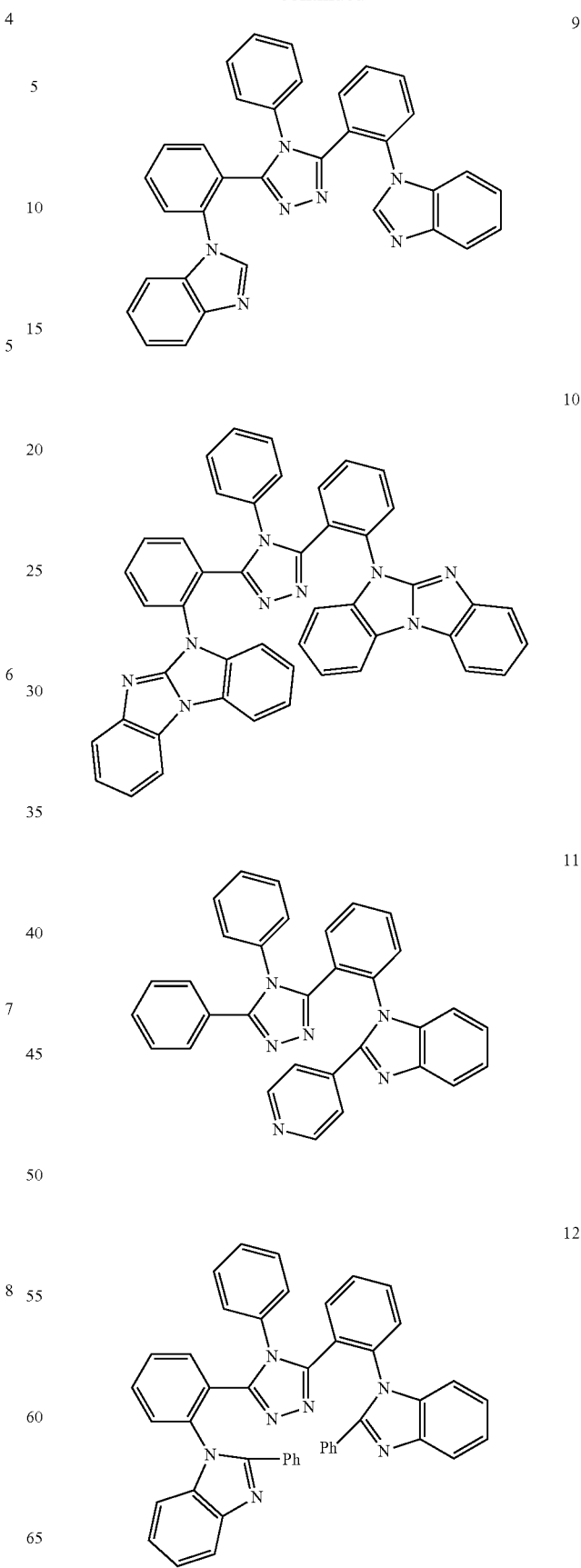

13
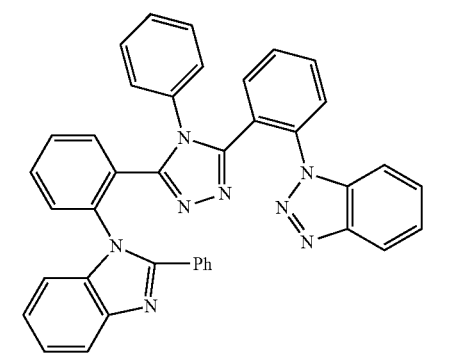
14
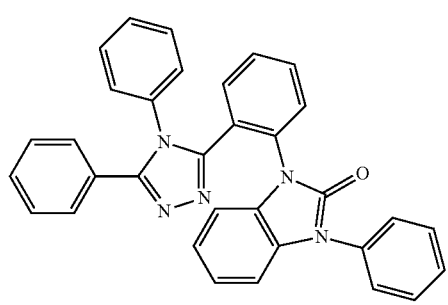
15
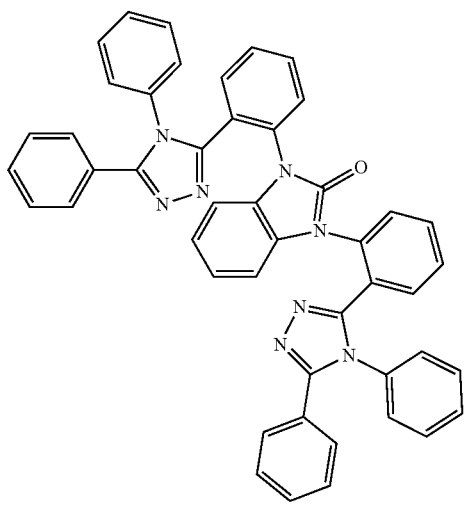
16
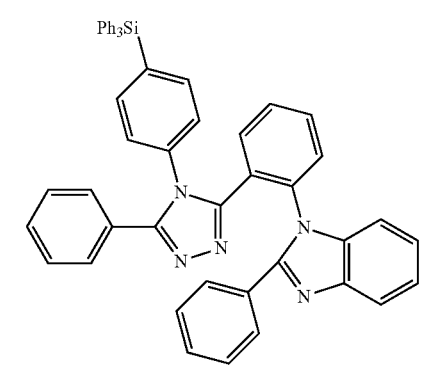
17
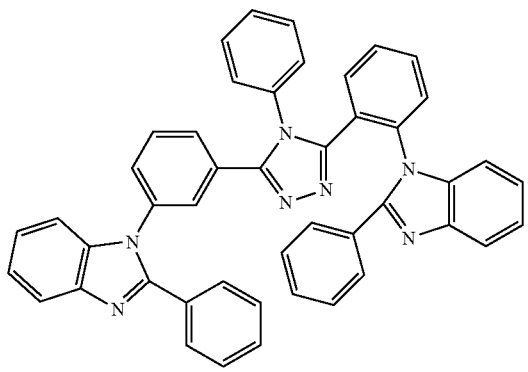
18
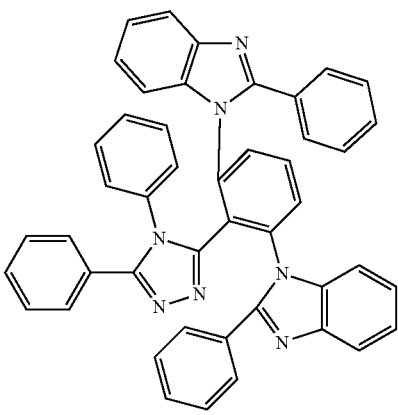
19
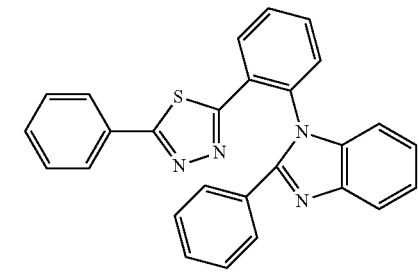
20
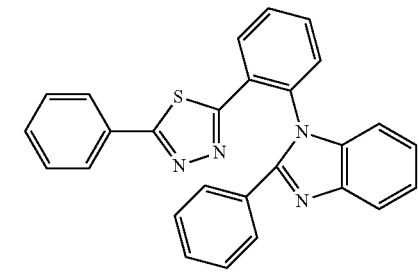
21

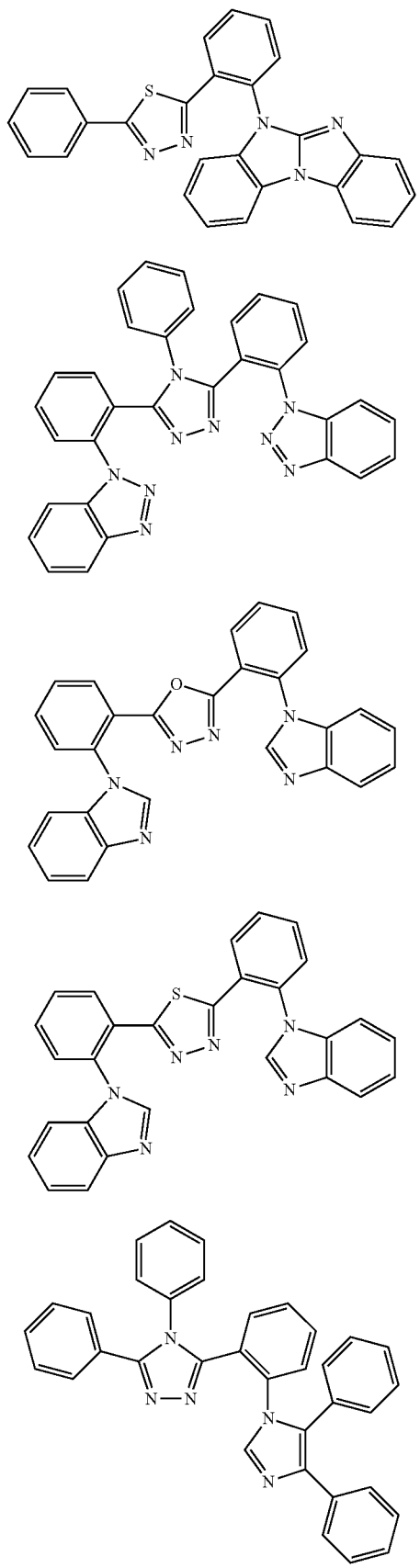
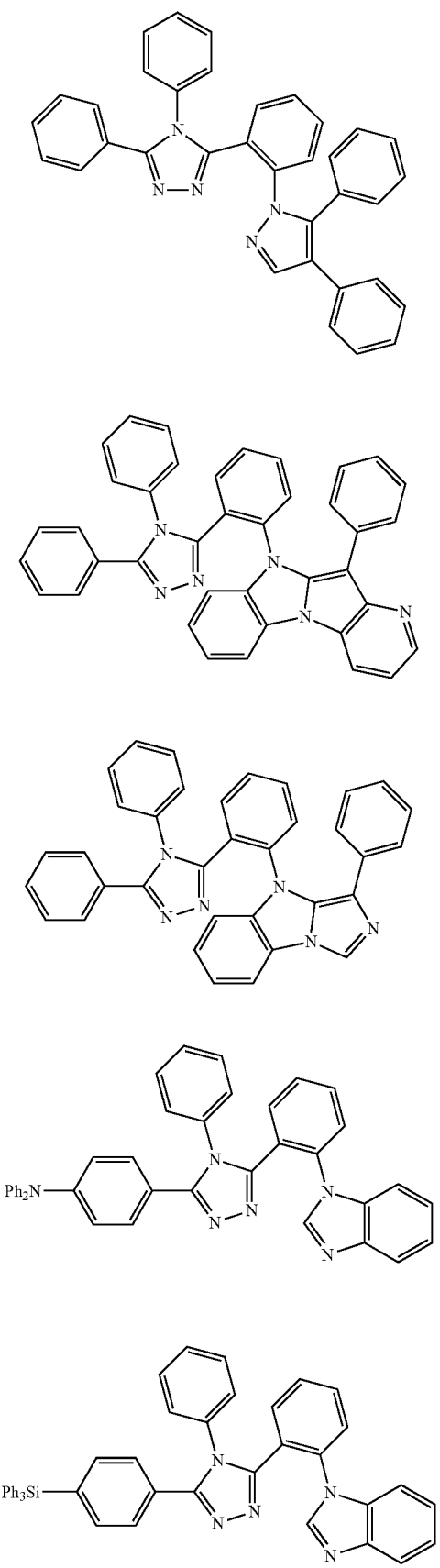

-continued

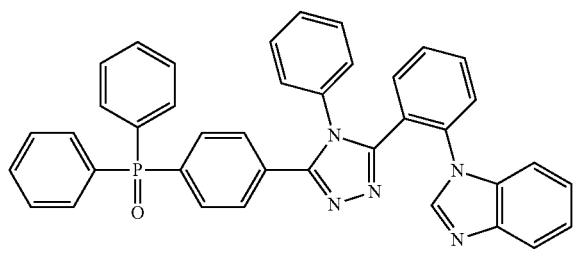
32

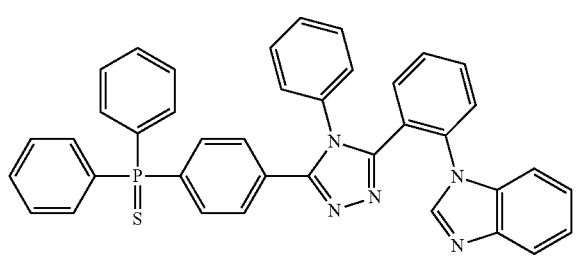
33

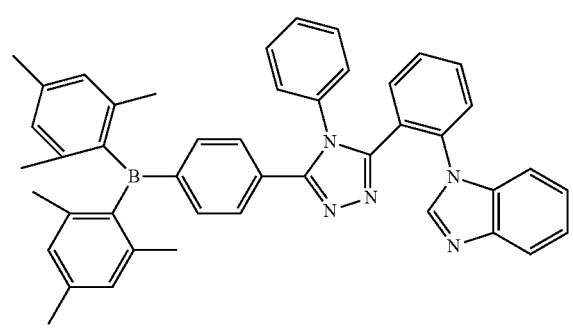
34

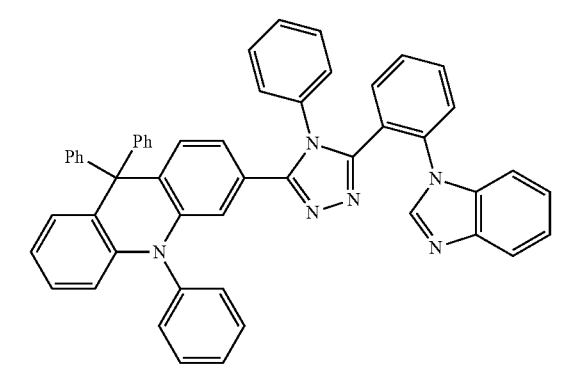
35

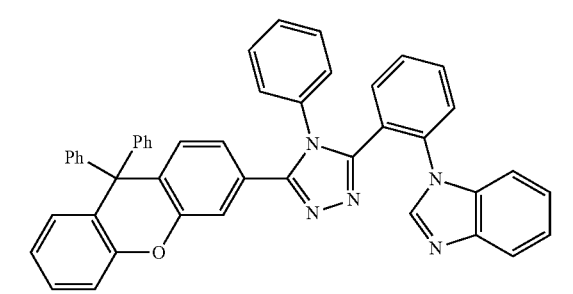
36

-continued

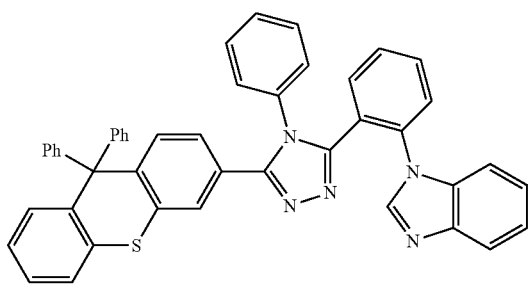
37

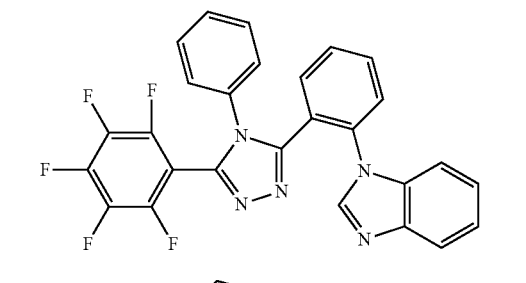
38

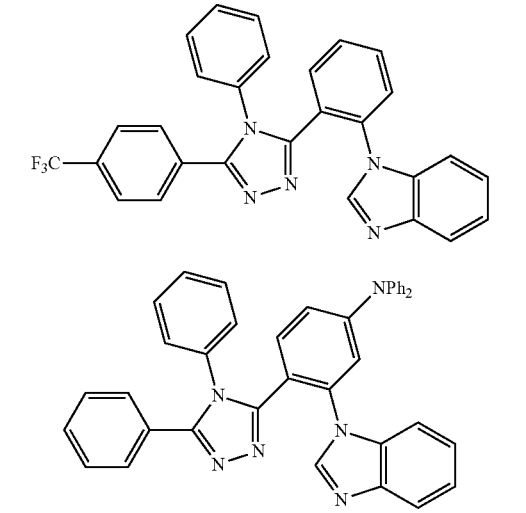
39

40

41

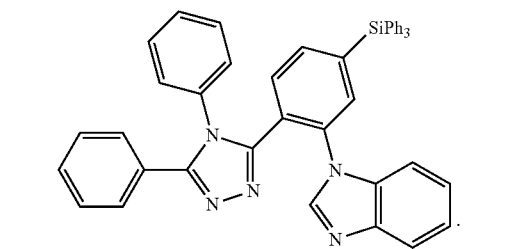

In the above structures, Ph may refer to a phenyl group.

The compound including nitrogen according to an embodiment of the present disclosure has a triazole, oxadiazole or thiadiazole skeleton (e.g., moiety), and has a structure in which an electron accepting substituent is at an ortho position on a benzene ring to the position at which the skeleton (e.g., above-described moiety) is substituted. By substituting two kinds of five-membered rings including nitrogen at an ortho position on a benzene ring, the resulting molecular structure may be distorted and the lowest triplet energy level may be increased. Accordingly, the compound including nitrogen according to an embodiment of the present disclosure may be easily applied as a phosphorescence host material. If the compound including nitrogen according to an embodiment of the present disclosure is used as the phosphorescence host material, high charge mobility may be attained, and at the same time, the trapping of the lowest triplet energy level of a dopant may be possible.

The compound including nitrogen according to an embodiment of the present disclosure may have the lowest triplet energy level (T1) of about 3.0 eV or more.

Referring to FIG. 1 to FIG. 3 again, an organic electroluminescence device according to an embodiment of the present disclosure will be explained.

Hereinafter, the above-described compound including nitrogen according to an embodiment of the present disclosure will be explained primarily with respect to different features, and unexplained parts will follow the above explanation in connection with the compound including nitrogen according to an embodiment of the present disclosure.

The first electrode EL1 has conductivity. The first electrode EL1 may be a pixel electrode or an anode. The first electrode EL1 may be a transmissive electrode, a transflective electrode, or a reflective electrode. If the first electrode EL1 is the transmissive electrode, the first electrode EL1 may be formed using a transparent metal oxide such as indium tin oxide (ITO), indium zinc oxide (IZO), zinc oxide (ZnO), and/or indium tin zinc oxide (ITZO). If the first electrode EL1 is the transflective electrode or the reflective electrode, the first electrode EL1 may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). Also, the first electrode EL1 may include a plurality of layers including the reflective layer and/or transflective layer formed using any of the above materials, or a transparent layer formed using ITO, IZO, ZnO, and/or ITZO. For example, the first electrode EL1 may have a three-layer structure of ITO/Ag/ITO, but an embodiment of the present disclosure is not limited thereto.

The thickness of the first electrode EL1 may be from about 1,000 Å to about 10,000 Å, for example, from about 1,000 Å to about 3,000 Å.

The hole transport region HTR is provided on the first electrode EL1. The hole transport region HTR may include at least one of a hole injection layer HIL, a hole transport layer HTL, a hole buffer layer, or an electron blocking layer.

The hole transport region HTR may have a single layer formed using a single material, a single layer formed using a plurality of different materials, or a multilayer structure including a plurality of layers formed using a plurality of different materials.

For example, the hole transport region HTR may have the structure of a single layer such as a hole injection layer HIL, or a hole transport layer HTL, and may have a structure of a single layer formed using a hole injection material and a hole transport material. In an embodiment, the hole transport region HTR may have a structure of a single layer formed using a plurality of different materials, or a structure, laminated from the first electrode EL1, of hole injection layer HIL/hole transport layer HTL, hole injection layer HIL/hole transport layer HTL/hole buffer layer, hole injection layer HIL/hole buffer layer, hole transport layer HTL/hole buffer layer, or hole injection layer HIL/hole transport layer HTL/electron blocking layer, without limitation.

The hole transport region HTR may be formed using various methods such as a vacuum deposition method, a spin coating method, a cast method, a Langmuir-Blodgett (LB) method, an inkjet printing method, a laser printing method, and/or a laser induced thermal imaging (LITI) method.

The hole injection layer HIL may include, for example, a phthalocyanine compound (such as copper phthalocyanine); N,N'-diphenyl-N,N'-bis-[4-(phenyl-m-tolyl-amino)-phenyl]-biphenyl-4,4'-diamine (DNTPD), 4,4',4"-tris(3-methylphenylphenylamino) triphenylamine (m-MTDATA), 4,4',4"-tris(N,N-diphenylamino)triphenylamine (TDATA), 4,4',4"-tris{N-(2-naphthyl)-N-phenylamino}-triphenylamine (2-TNATA), poly(3,4-ethylenedioxythiophene)/poly(4-styrenesulfonate) (PEDOT/PSS), polyaniline/dodecylbenzenesulfonic acid (PANI/DBSA), polyaniline/camphor sulfonic acid (PANI/CSA), polyaniline/poly(4-styrenesulfonate) (PANI/PSS), N,N'-di(naphthalene-1-yl)-N,N'-diphenyl-(1,1'-benzidine) (NPD), triphenylamine-containing polyether ketone (TPAPEK), 4-isopropyl-4'-methyldiphenyliodonium tetrakis(pentafluorophenyl)borate, tetrakis(pentafluorophenyl)borate, 1,4,5,8,9,11-hexaazatriphenylenehexacarbonitrile (HAT-CN), etc., without limitation.

The hole transport layer HTL may include, for example, carbazole derivatives (such as N-phenyl carbazole and/or polyvinyl carbazole), fluorine-based derivatives, N,N'-bis(3-methylphenyl)-N,N'-diphenyl-[1,1-biphenyl]-4,4'-diamine (TPD), triphenylamine-based derivatives (such as 4,4',4"-tris(N-carbazolyl)triphenylamine (TCTA)), N,N'-di(1-naphthalene-1-yl)-N,N'-diphenyl-benzidine (NPB), 4,4'-cyclohexylidene bis[N,N-bis(4-methylphenyl)benzenamine] (TAPC), 4,4'-bis[N,N'-(3-tolyl)amino]-3,3'-dimethylbiphenyl (HMTPD), etc., without limitation.

The electron blocking layer EBL may include, for example, commonly known materials in the art. The electron blocking layer EBL may include, for example, carbazole derivatives (such as N-phenyl carbazole and/or polyvinyl carbazole), fluorine-based derivatives, N,N'-bis(3-methylphenyl)-N,N'-diphenyl-[1,1-biphenyl]-4,4'-diamine (TPD), triphenylamine-based derivatives (such as 4,4',4"-tris(N-carbazolyl)triphenylamine (TCTA)), N,N'-di(1-naphthalene-1-yl)-N,N'-diphenyl-benzidine (NPB), 4,4'-cyclohexylidene bis[N,N-bis(4-methylphenyl)benzenamine] (TAPC), 4,4'-bis[N,N'-(3-tolypamino]-3,3'-dimethylbiphenyl (HMTPD), mCP, etc., without limitation. In addition, as described above, the electron blocking layer EBL may include the compound including nitrogen according to an embodiment of the present disclosure.

The thickness of the hole transport region HTR may be from about 100 Å to about 10,000 Å, for example, from about 100 Å to about 5,000 Å. The thickness of the hole injection layer HIL may be from about 30 Å to about 1,000 Å, and the thickness of the hole transport layer HTL may be from about 30 Å to about 1,000 Å. For example, the thickness of the electron blocking layer EBL may be from about 10 Å to about 1,000 Å. If the thicknesses of the hole transport region HTR, the hole injection layer HIL, the hole transport layer HTL and the electron blocking layer EBL satisfy the above-described ranges, satisfactory (or suitable) hole transport properties may be obtained without substantial increase of a driving voltage.

The hole transport region HTR may further include a charge generating material, in addition to the above-described materials, to increase conductivity. The charge generating material may be dispersed uniformly or non-uniformly in the hole transport region HTR. The charge generating material may be, for example, a p-dopant. The p-dopant may be one of quinone derivatives, metal oxides, or cyano group-containing compounds, without limitation. Non-limiting examples of the p-dopant may include quinone derivatives (such as tetracyanoquinodimethane (TCNQ) and/or 2,3,5,6-tetrafluoro-tetracyanoquinodimethane (F4-

TCNQ)), metal oxides (such as tungsten oxide and/or molybdenum oxide), without limitation.

As described above, the hole transport region HTR may further include at least one of a hole buffer layer or an electron blocking layer. The hole buffer layer may compensate a resonance distance according to the wavelength of light emitted from the emission layer EML and increase light emission efficiency. Any of the materials included in the hole transport region HTR may be used as materials included in the hole buffer layer. The electron blocking layer is a layer preventing (or reducing) electron injection from the electron transport region ETR to the hole transport region HTR.

The emission layer EML is provided on the hole transport region HTR. The emission layer EML may have a thickness of, for example, from about 100 Å to about 1,000 Å, or from about 100 Å to about 300 Å. The emission layer EML may have a single layer formed using a single material, a single layer formed using a plurality of different materials, or a multilayer structure having a plurality of layers formed using a plurality of different materials.

The emission layer EML may include the compound including nitrogen according to an embodiment of the present disclosure.

The emission layer EML may include one, two or more of the compounds including nitrogen represented by Formula 1. The emission layer EML may further include a known material, in addition to the compound including nitrogen represented by Formula 1. For example, the emission layer EML may further include a material including any one selected from spiro-DPVBi, 2,2',7,7'-tetrakis(biphenyl-4-yl)-9,9'-spirobifluorene(spiro-sexiphenyl)) (spiro-6P), distyryl-benzene (DSB), distyryl-arylene (DSA), a polyfluorene (PFO)-based polymer and a poly(p-phenylene vinylene (PPV)-based polymer. However, embodiments of the present disclosure are not limited thereto.

The emission layer EML may include a host and a dopant. The host may include the compound including nitrogen according to an embodiment of the present disclosure, and the dopant may be a phosphorescence dopant. For example, the compound including nitrogen according to an embodiment of the present disclosure may be used as a phosphorescence host material. However, embodiments of the present disclosure are not limited thereto. For example, the compound including nitrogen according to an embodiment of the present disclosure may be used as a material for thermally activated delayed fluorescence.

The emission layer EML may be, for example, a blue emission layer emitting blue light. However, an embodiment of the present disclosure is not limited thereto, and the EML may be a layer emitting red light or green light.

The host may further include host materials known in the art, in addition to the compound including nitrogen according to an embodiment of the present disclosure. For example, tris(8-hydroxyquinolino)aluminum ($Alq_3$), 4,4'-bis(N-carbazolyl)-1,1'-biphenyl (CBP), poly(N-vinylcarbazole) (PVK), 9,10-di(naphthalene-2-yl)anthracene (ADN), 4,4',4''-tris(carbazol-9-yl)-triphenylamine (TCTA), 1,3,5-tris(N-phenylbenzimidazole-2-yl)benzene (TPBi), 3-tert-butyl-9,10-di(naphth-2-yl)anthracene (TBADN), distyrylarylene (DSA), 4,4'-bis(9-carbazolyl)-2,2'-dimethyl-biphenyl (CDBP), 2-methyl-9,10-bis(naphthalen-2-yl)anthracene (MADN), bis[2-(diphenylphosphino)phenyl]ether oxide (DPEPO), hexaphenyl cyclotriphosphazene (CP1), 1,4-bis(triphenylsilyl)benzene (UGH2), hexaphenylcyclotrisiloxane ($DPSiO_3$), octaphenylcyclotetra siloxane ($DPSiO_4$), 2,8-bis(diphenylphosphoryl)dibenzofuran (PPF), etc., without limitation, may be further included.

The dopant may include materials known in the art. For example, a metal complex including at least one of iridium (Ir), platinum (Pt), palladium (Pd), osmium (Os), titanium (Ti), zirconium (Zr), hafnium (Hf), europium (Eu), terbium (Tb), rhodium (Rh) or thulium (Tm), may be included. For example, bis[2-(4,6-difluorophenyl)pyridinato-C2,N](picolinato)iridium(III) (Flrpic) may be included. The dopant may be a fluorescence dopant. The fluorescence dopant may include, for example, an arylamine compound or a styrylamine compound.

The electron transport region ETR is provided on the emission layer EML. The electron transport region ETR may include at least one of a hole blocking layer HBL, an electron transport layer ETL, or an electron injection layer EIL, without limitation.

The electron transport region ETR may have a single layer formed using a single material, a single layer formed using a plurality of different materials, or a multilayer structure having a plurality of layers formed using a plurality of different materials.

For example, the electron transport region ETR may have a single layer structure of an electron injection layer EIL or an electron transport layer ETL, or a single layer structure formed using an electron injection material and an electron transport material. Further, the electron transport region ETR may have a single layer structure having a plurality of different materials, or a structure, laminated from the emission layer EML, of electron transport layer ETL/electron injection layer EIL, or hole blocking layer HBL/electron transport layer ETL/electron injection layer EIL, without limitation. The thickness of the electron transport region ETR may be, for example, from about 1,000 Å to about 1,500 Å.

The electron transport region ETR may be formed using various methods such as a vacuum deposition method, a spin coating method, a cast method, a Langmuir-Blodgett (LB) method, an inkjet printing method, a laser printing method, and/or a laser induced thermal imaging (LITI) method.

If the electron transport region ETR includes an electron transport layer ETL, the electron transport region ETR may include tris(8-hydroxyquinolinato)aluminum ($Alq_3$), 1,3,5-tri[(3-pyridyl)-phen-3-yl]benzene, 2,4,6-tris(3'-(pyridin-3-yl)biphenyl-3-yl)-1,3,5-triazine, bis[2-(diphenylphosphino)phenyl]ether oxide (DPEPO), 2-(4-(N-phenylbenzoimidazolyl-1-ylphenyl)-9,10-dinaphthylanthracene, 1,3,5-tri(1-phenyl-1H-benzo[d]imidazol-2-yl)benzene (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,O8)-(1,1'-biphenyl-4-olato)aluminum (BAlq), berylliumbis(benzoquinolin-10-olate (Bebq2), 9,10-di(naphthalene-2-yl)anthracene (ADN), and/or a mixture thereof. However, an embodiment of the present disclosure is not limited thereto. The thickness of the electron transport layer ETL may be from about 100 Å to about 1,000 Å, for example, from about 150 Å to about 500 Å. If the thickness of the electron transport layer ETL satisfies the above-described range, satisfactory (or suitable) electron transport properties may be obtained without substantial increase of a driving voltage.

If the electron transport region ETR includes the electron injection layer EIL, the electron transport region ETR may use LiF, lithium quinolate (LiQ), $Li_2O$, BaO, NaCl, CsF, a metal in lanthanides such as Yb, or a metal halide such as RbCl, and/or RbI. However, an embodiment of the present disclosure is not limited thereto. The electron injection layer EIL also may be formed using a mixture material of an electron transport material and an insulating organo metal salt. The organo metal salt may be a material having an energy band gap of about 4 eV or more. The organo metal salt may include, for example, metal acetates, metal benzoates, metal acetoacetates, metal acetylacetonates, and/or metal stearates. The thickness of the electron injection layer EIL may be from about 1 Å to about 100 Å, from 3 Å to about 90 Å. If the thickness of the electron injection layer EIL satisfies the above-described range, satisfactory (or suitable) electron transport properties may be obtained without substantial increase of a driving voltage.

The electron transport region ETR may include a hole blocking layer HBL as described above. The hole blocking layer HBL may include, for example, 2,9-dimethyl-4,7-diphenyl-1,10-phenanthroline (BCP), 4,7-diphenyl-1,10-phenanthroline (Bphen), and/or bis[2-(diphenylphosphino)phenyl]ether oxide (DPEPO). However, an embodiment of the present disclosure is not limited thereto.

The second electrode EL2 is provided on the electron transport region ETR.

The second electrode EL2 may be a common electrode or a cathode. The second electrode EL2 may be a transmissive electrode, a transflective electrode or a reflective electrode. If the second electrode EL2 is the transmissive electrode, the second electrode EL2 may include a transparent metal oxide, for example, ITO, IZO, ZnO, ITZO, etc., without limitation.

If the second electrode EL2 is the transflective electrode or the reflective electrode, the second electrode EL2 may include, for example, Ag, Mg, Cu, Al, Pt, Pd, Au, Ni, Nd, Ir, Cr, Li, Ca, LiF/Ca, LiF/Al, Mo, Ti, a compound including thereof, or a mixture thereof (for example, a mixture of Ag and Mg). The second electrode EL2 may have a multilayered structure including a reflective layer or a transflective layer formed using any of the above-described materials and a transparent conductive layer formed using ITO, IZO, ZnO, ITZO, etc.

Though not shown, the second electrode EL2 may be connected with an auxiliary electrode. If the second electrode EL2 is connected with the auxiliary electrode, the resistance of the second electrode EL2 may decrease.

In the organic electroluminescence device 10, according to the application of a voltage to each of the first electrode EL1 and second electrode EL2, holes injected from the first electrode EL1 may move via the hole transport region HTR to the emission layer EML, and electrons injected from the second electrode EL2 may move via the electron transport region ETR to the emission layer EML. The electrons and the holes are recombined in the emission layer EML to produce excitons, and the excitons may emit light via transition from an excited state to a ground state.

If the organic electroluminescence device 10 is a top emission device, the first electrode EL1 may be a reflective electrode and the second electrode EL2 may be a transmissive electrode or a transflective electrode. If the organic electroluminescence device 10 is a bottom emission device, the first electrode EL1 may be a transmissive electrode or a transflective electrode and the second electrode EL2 may be a reflective electrode.

When the organic electroluminescence device 10 according to an embodiment of the present disclosure includes the compound including nitrogen represented by Formula 1, high emission efficiency may be achieved.

Hereinafter, the present disclosure will be explained in more detail with reference to particular preparation methods, embodiments and comparative embodiments. The following embodiments are only illustrations to assist in the understanding of the present disclosure, and the scope of the present disclosure is not limited thereto.

SYNTHETIC EXAMPLES

The compound including nitrogen according to example embodiments of the present disclosure may be synthesized, for example, as follows. However, embodiments of the present disclosure are not limited thereto.

1. Synthesis of Compound 1

Compound 1, which is the compound including nitrogen according to an embodiment of the present disclosure, may be synthesized, for example, by the reaction below.

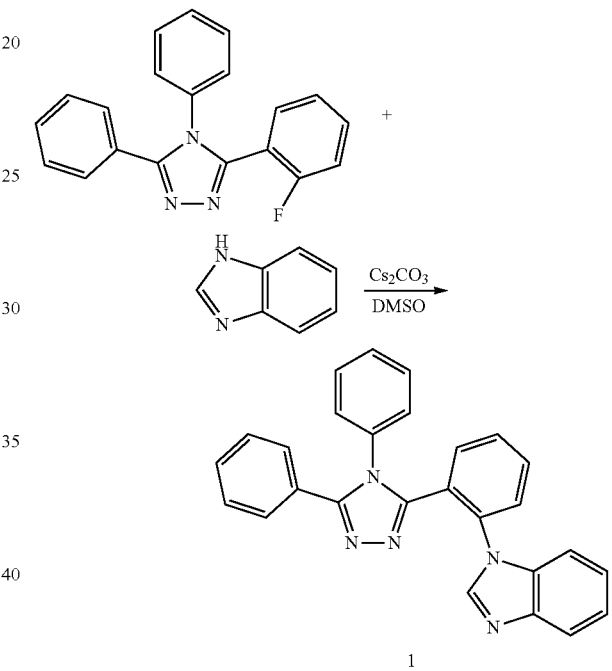

Under an argon (Ar) atmosphere, to a 200 ml three-neck flask, 4.62 g (14.6 mmol) of 3-(2-fluorophenyl)-4,5-diphenyl-4H-1,2,4-triazole, 1.73 g (14.6 mmol) of benzimidazole, 9.54 g (29.3 mmol) of $Cs_2CO_3$, and 44 ml of DMSO were added and stirred at about 160° C. for about 2 hours. After cooling the resulting mixture in the air, water was added thereto, and white precipitation thus produced were filtered and taken. The crude product thus obtained was separated by silica gel column chromatography, and 5.36 g (yield 89%) of Compound 1 was obtained as a white solid.

The molecular weight of Compound 1 measured by Fast Atom Bombardment Mass Spectrometry (FAB-MS) was 413. The chemical shift (δ) values of Compound 1 measured by $^1$H-NMR ($CDCl_3$) were 8.04 (1H), 7.70-7.60 (3H), 7.48 (1H), 7.38 (1H), 7.29 (1H), 7.23-7.16 (5H), 7.06 (1H), 6.97 (1H), 6.82-6.73 (3H), 6.19 (2H).

2. Synthesis of Compound 7

Compound 7, which is the compound including nitrogen according to an embodiment of the present disclosure, may be synthesized, for example, by the reaction below.

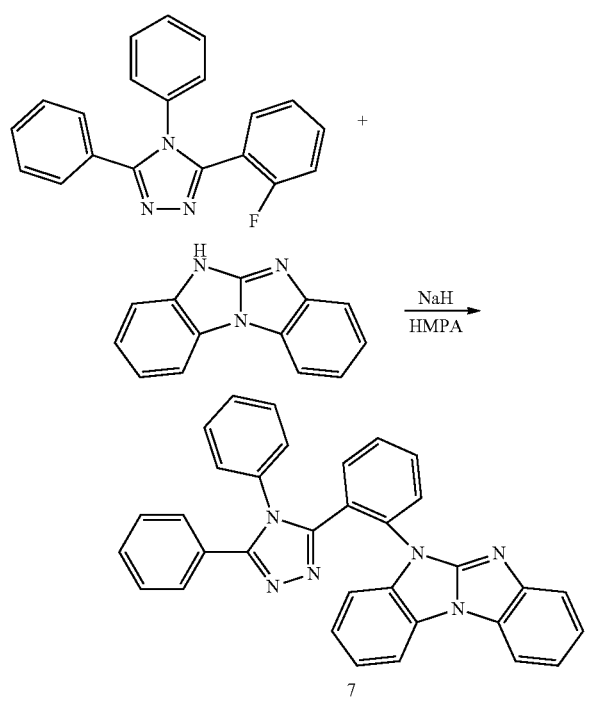

7

Under an argon (Ar) atmosphere, to a 200 ml three-neck flask, 3.64 g (11.5 mmol) of 3-(2-fluorophenyl)-4,5-diphenyl-4H-1,2,4-triazole, 2.38 g (11.5 mmol) of 5H-benzimidazolo[1,2-a]benzimidazole, 0.703 g (29.3 mmol) of NaH, and 58 ml of HPMA were added and stirred at about 200° C. for about 12 hours. After cooling the resulting mixture in the air, water was added thereto, and white precipitation thus produced were filtered and taken. The crude product thus obtained was separated by silica gel column chromatography, and 2.83 g (yield 49%) of Compound 7 was obtained as a white solid.

The molecular weight of Compound 7 measured by FAB-MS was 502. The chemical shift (δ) values of Compound 7 measured by $^1$H-NMR (CDCl$_3$) were 8.58-8.54 (3H), 8.28 (2H), 7.82-7.75 (2H), 7.68-7.46 (9H), 7.38 (2H), 7.30-7.19 (4H).

3. Synthesis of Compound 9

Compound 9, which is the compound including nitrogen according to an embodiment of the present disclosure, may be synthesized, for example, by the reaction below.

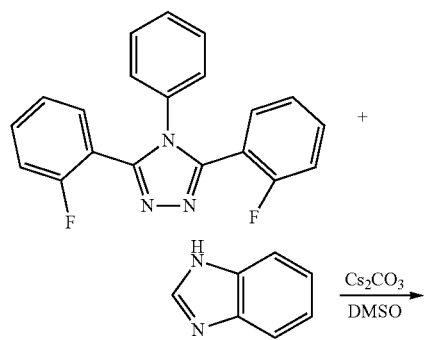

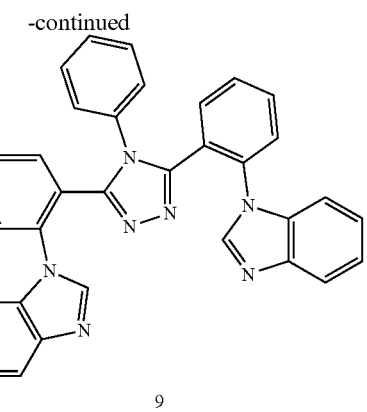

9

Under an argon (Ar) atmosphere, to a 200 ml three-neck flask, 3.34 g (10.0 mmol) of 3,5-bis(2-fluorophenyl)-4-phenyl-4H-1,2,4-triazole, 2.36 g (20.0 mmol) of benzimidazole, 13.03 g (40.0 mmol) of Cs$_2$CO$_3$, and 60 ml of DMSO were added and stirred at about 160° C. for about 2 hours. After cooling the resulting mixture in the air, water was added thereto, and white precipitation thus produced were filtered and taken. The crude product thus obtained was separated by silica gel column chromatography, and 4.29 g (yield 81%) of Compound 9 was obtained as a white solid.

The molecular weight of Compound 9 measured by FAB-MS was 529. The chemical shift (δ) values of Compound 9 measured by $^1$H-NMR (CDCl$_3$) were 8.56 (2H), 8.08 (2H), 7.82-7.75 (4H), 7.68-7.19 (15H).

4. Synthesis of Compound 12

Compound 12, which is the compound including nitrogen according to an embodiment of the present disclosure, may be synthesized, for example, by the reaction below.

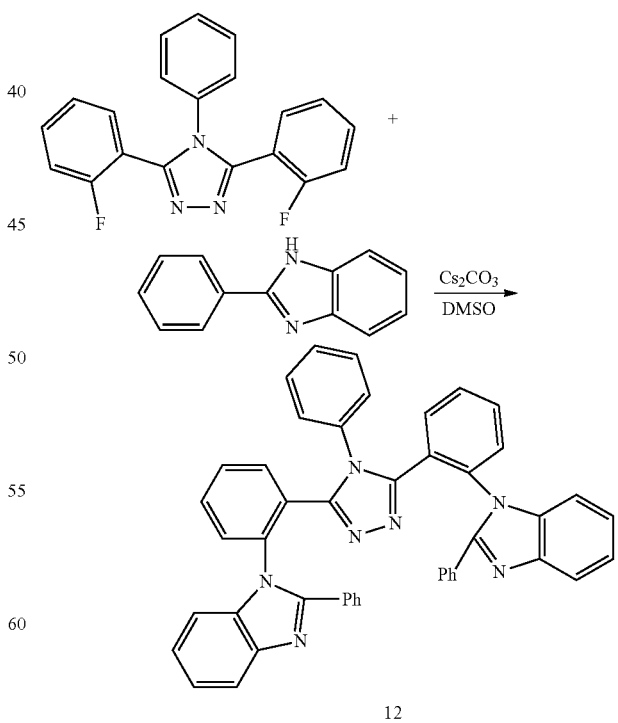

12

Under an argon (Ar) atmosphere, to a 200 ml three-neck flask, 3.34 g (10.0 mmol) of 3,5-bis(2-fluorophenyl)-4- phenyl-4H-1,2,4-triazole, 3.88 g (20.0 mmol) of 2-phenyl-benzimidazole, 13.03 g (40.0 mmol) of Cs$_2$CO$_3$, and 60 ml of DMSO were added and stirred at about 160° C. for about 2 hours. After cooling the resulting mixture in the air, water was added thereto, and white precipitation thus produced were filtered and taken. The crude product thus obtained was separated by silica gel column chromatography, and 6.27 g (yield 92%) of Compound 12 was obtained as a white solid.

The molecular weight of Compound 12 measured by FAB-MS was 681. The chemical shift (δ) values of Compound 12 measured by $^1$H-NMR (CDCl$_3$) were 8.56 (2H), 8.28 (4H), 7.83-7.75 (6H), 7.68-7.46 (15H), 7.38 (2H), 7.28 (2H).

5. Synthesis of Compound 21

Compound 21, which is the compound including nitrogen according to an embodiment of the present disclosure, may be synthesized, for example, by the reaction below.

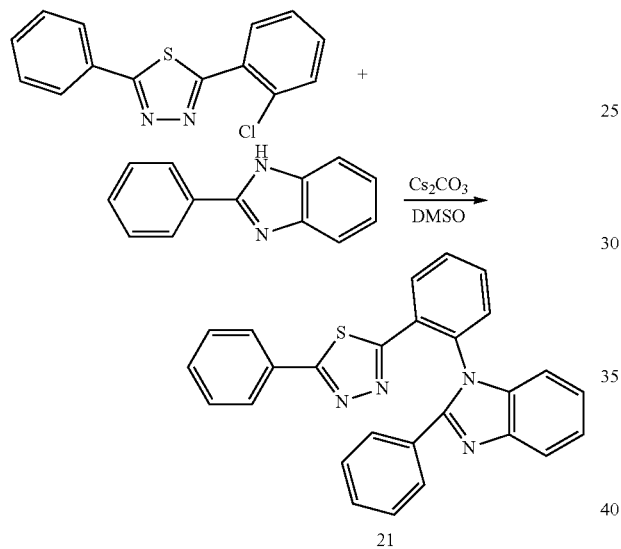

21

Under an argon (Ar) atmosphere, to a 200 ml three-neck flask, 3.11 g (11.4 mmol) of 2-(2-chlorophenyl)-5-phenyl-1,3,4-thiadiazole, 2.21 g (11.4 mmol) of 2-phenylbenzimidazole, 7.43 g (22.8 mmol) of Cs$_2$CO$_3$, and 23 ml of DMSO were added and stirred at about 180° C. for about 12 hours. After cooling the resulting mixture in the air, water was added thereto, and white precipitation thus produced were filtered and taken. The crude product thus obtained was separated by silica gel column chromatography, and 3.53 g (yield 72%) of Compound 21 was obtained as a white solid.

The molecular weight of Compound 21 measured by FAB-MS was 430. The chemical shift (δ) values of Compound 21 measured by $^1$H-NMR (CDCl$_3$) were 8.56 (1H), 8.28 (2H), 8.03 (2H), 7.83-7.75 (3H), 7.66 (1H), 7.55-7.48 (8H), 7.28 (1H).

The above-described synthetic examples are example embodiments, and reaction conditions may be changed according to need. In addition, the compound according to an embodiment of the present disclosure may be synthesized so as to have various substituents using known methods and materials. By introducing various substituents to the core structure represented by Formula 1, appropriate properties for an organic electroluminescence device may be attained.

(Device Manufacturing Examples)

Organic electroluminescence devices of Examples 1 to 5 were manufactured using each of Compounds 1, 7, 9, 12 and 21 as the host material of an emission layer.

Example Compounds

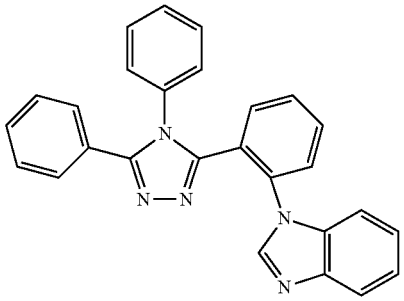

1

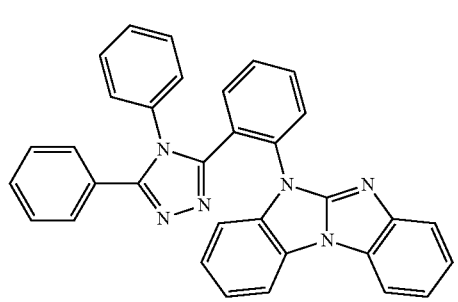

7

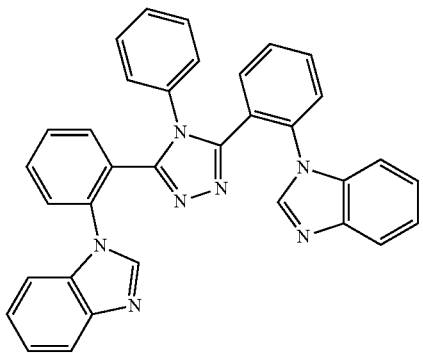

9

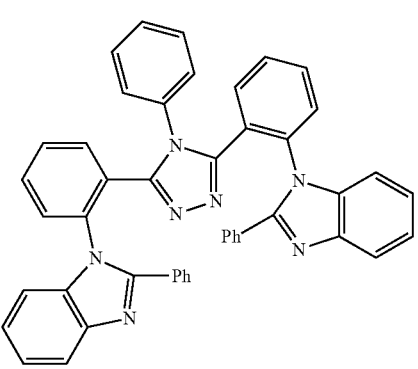

12

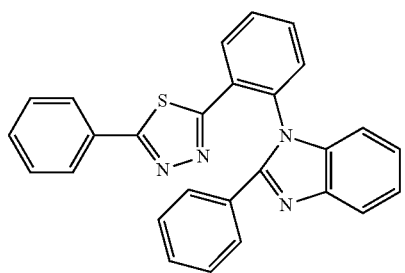

Using each of Comparative Compounds c1 to c7 as the host material of an emission layer, organic electroluminescence devices of Comparative Examples 1 to 7 were manufactured.

Comparative Compounds

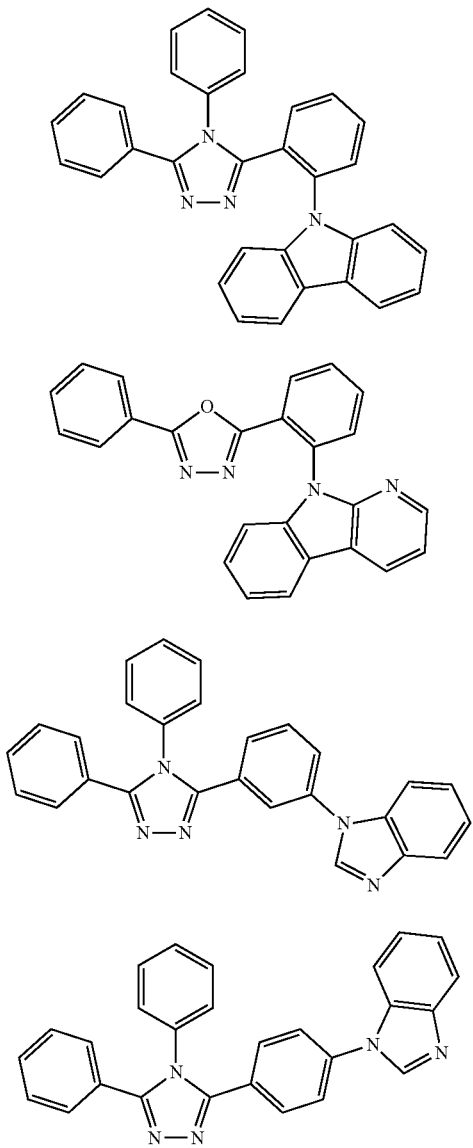

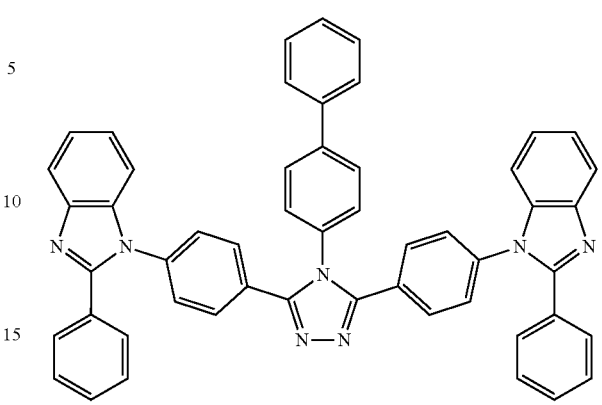

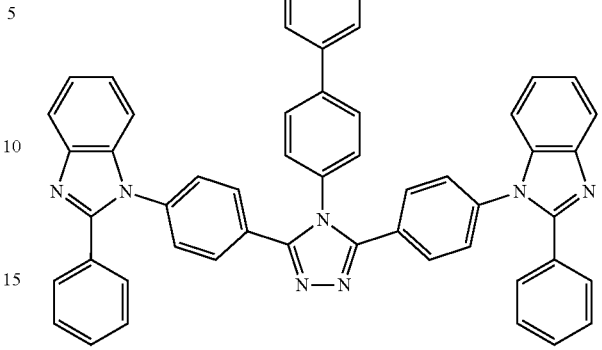

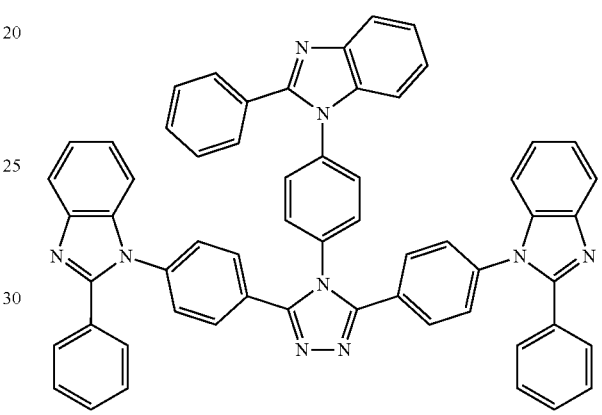

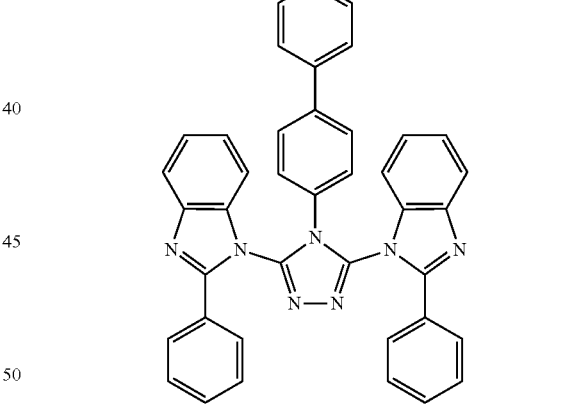

Organic electroluminescence devices of Examples 1 to 5 and Comparative Examples 1 to 7 were manufactured by forming a first electrode using ITO to a thickness of about 150 nm, a hole injection layer using HAT-CN to a thickness of about 10 nm, a hole transport layer using NPB to a thickness of about 40 nm, an electron blocking layer using mCP to a thickness of about 10 nm, an emission layer using the respective example compound or the comparative compound doped with 8% Flrpic to a thickness of about 20 nm, a hole blocking layer using DPEPO to a thickness of about 10 nm, an electron transport layer using TPBi to a thickness of about 30 nm, an electron injection layer using LiF to a thickness of about 2 nm, and a second electrode using Al to a thickness of about 120 nm. Each layer was formed by a deposition method under vacuum.

TABLE 1

| | Host material of emission layer | Maximum emission efficiency |
|---|---|---|
| Example 1 | Example Compound 1 | 130% |
| Example 2 | Example Compound 7 | 120% |
| Example 3 | Example Compound 9 | 130% |
| Example 4 | Example Compound 12 | 110% |
| Example 5 | Example Compound 21 | 110% |
| Comparative Example 1 | Comparative Compound c1 | 100% |
| Comparative Example 2 | Comparative Compound c2 | 105% |
| Comparative Example 3 | Comparative Compound c3 | 80% |
| Comparative Example 4 | Comparative Compound c4 | 70% |
| Comparative Example 5 | Comparative Compound c5 | 50% |
| Comparative Example 6 | Comparative Compound c6 | 80% |
| Comparative Example 7 | Comparative Compound c7 | 60% |

The maximum emission efficiency is represented by % on the basis of Comparative Example 1.

Referring to Table 1, Examples 1 to 5 had increased efficiency when compared to Comparative Examples 1 to 7. In Comparative Examples 1 and 2, since carbazole or carboline is substituted at an ortho position on a phenyl group which is substituted for triazole or oxadiazole, the lowest triplet energy level was decreased, and emission efficiency was reduced. In addition, in Comparative Examples 3 to 6, since the substitution position of benzoimidazole is meta or para position, the distortion of a molecule was decreased, and a triplet energy level was decreased and emission efficiency was deteriorated. Meanwhile, in Comparative Examples 5 and 7, a biphenyl group is included in a molecule, and the lowest triplet energy level was decreased, and as a result, emission efficiency was reduced.

The compound including nitrogen according to an embodiment of the present disclosure may be used in an emission layer, and the emission efficiency of an organic electroluminescence device may be improved.

The compound including nitrogen according to an embodiment of the present disclosure may be used in an emission layer, and the life of an organic electroluminescence device may be increased.

The organic electroluminescence device according to an embodiment of the present disclosure has excellent efficiency.

The compound including nitrogen according to an embodiment of the present disclosure may be applied to an organic electroluminescence device and may contribute to efficiency improvement.

As used herein, the terms "substantially," "about," and similar terms are used as terms of approximation and not as terms of degree, and are intended to account for the inherent deviations in measured or calculated values that would be recognized by those of ordinary skill in the art.

Also, any numerical range recited herein is intended to include all subranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

Although the example embodiments of the present invention have been described, it is understood that the present invention should not be limited to these example embodiments but various changes and modifications can be made by one ordinary skilled in the art within the spirit and scope of the present invention as defined by the following claims and equivalents thereof.

What is claimed is:

1. An organic electroluminescence device, comprising:
a first electrode;
a hole transport region on the first electrode;
an emission layer on the hole transport region;
an electron transport region on the emission layer; and
a second electrode on the electron transport region,
wherein the first electrode and the second electrode each independently comprise at least one selected from Ag, Mg, Cu, Al, Pt, Pd, Au, Ni, Nd, Ir, Cr, Li, Ca, LiF/Ca, LiF/Al, Mo, Ti, In, Sn, and Zn, a compound of two or more thereof, a mixture of two or more thereof, and an oxide thereof,
wherein the emission layer comprises a compound including nitrogen represented by Formula 1:

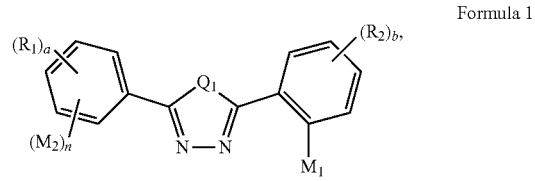

Formula 1 wherein in Formula 1,
$Q_1$ is $NAr_1$, O or S,
$Ar_1$ is a hydrogen atom, a deuterium atom, a substituted or unsubstituted aryl group having 6 to 30 carbon atoms for forming a ring, or a substituted or unsubstituted heteroaryl group having 2 to 30 carbon atoms for forming a ring,
$R_1$ and $R_2$ are each independently a hydrogen atom, a deuterium atom, a halogen atom, a substituted or unsubstituted amino group, a substituted or unsubstituted silyl group, a substituted or unsubstituted boryl group, a substituted or unsubstituted alkyl group having 1 to 10 carbon atoms, a substituted or unsubstituted aralkyl group having 6 to 30 carbon atoms, a substituted or unsubstituted haloalkyl group having 1 to 10 carbon atoms, a substituted or unsubstituted aryloxy group having 6 to 30 carbon atoms, a substituted or unsubstituted arylthio group having 6 to 30 carbon atoms, a substituted or unsubstituted phosphine oxy group, a substituted or unsubstituted phosphine sulfide group, a substituted or unsubstituted aryl group having 6 to 30 carbon atoms for forming a ring, or a substituted or unsubstituted heteroaryl group having 2 to 30 carbon atoms for forming a ring, and $R_1$ and $R_2$ are each independently optionally combined with an adjacent group to form a ring,
"a" and "b" are each independently an integer of 0 to 4,
"n" is 0 or 1, and $M_1$ and $M_2$ are each independently represented by Formulae 2 or 3:

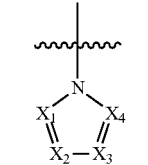

Formula 2

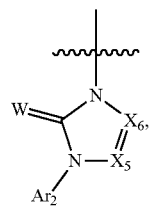

Formula 3 wherein in Formulae 2 and 3, $X_1$ to $X_6$ are each independently $CR_3$ or N, at least one of $X_1$ to $X_4$ is N, $R_3$ is a hydrogen atom, a deuterium atom, a substituted or unsubstituted alkyl group having 1 to 10 carbon atoms, a substituted or unsubstituted aryl group having 6 to 30 carbon atoms for forming a ring, or a substituted or unsubstituted heteroaryl group having 2 to 30 carbon atoms for forming a ring, and $R_3$ is optionally combined with an adjacent group to form a ring, W is O, $NAr_3$, or $CAr_4Ar_5$, $Ar_2$ to $Ar_5$ are each independently a hydrogen atom, a deuterium atom, a substituted or unsubstituted alkyl group having 1 to 10 carbon atoms, a substituted or unsubstituted aralkyl group, a substituted or unsubstituted aryl group having 6 to 30 carbon atoms for forming a ring, or a substituted or unsubstituted heteroaryl group having 2 to 30 carbon atoms for forming a ring, and $Ar_2$ to $Ar_5$ are each independently optionally combined with an adjacent group to form a ring.

2. The organic electroluminescence device of claim 1, wherein Formula 2 is represented by one of Formulae 2-1 to 2-3:

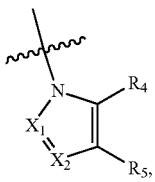

Formula 2-1

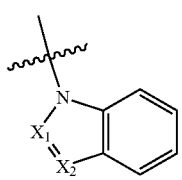

Formula 2-2

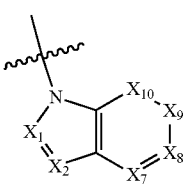

Formula 2-3 wherein in Formulae 2-1 to 2-3, $X_1$ and $X_2$ are each independently $CR_3$ or N, at least one of $X_1$ or $X_2$ is N, $X_7$ to $X_{10}$ are each independently $CR_6$ or N, at least one of $X_7$ to $X_{10}$ is N, and $R_3$ to $R_6$ are each independently a hydrogen atom, a substituted or unsubstituted aryl group having 6 to 30 carbon atoms for forming a ring, or a substituted or unsubstituted heteroaryl group having 2 to 30 carbon atoms for forming a ring.

3. The organic electroluminescence device of claim 1, wherein Formula 3 is represented by one of Formulae 3-1 to 3-4:

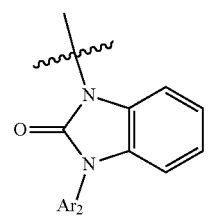

Formula 3-1

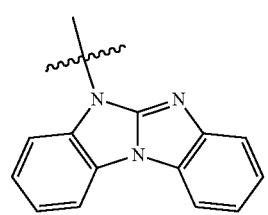

Formula 3-2

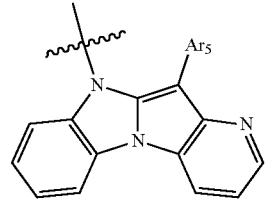

Formula 3-3

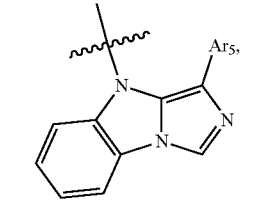

Formula 3-4 wherein in Formulae 3-1, 3-3 and 3-4, $Ar_2$ and $Ar_5$ are each independently a substituted or unsubstituted aryl group having 6 to 30 carbon atoms for forming a ring, or a substituted or unsubstituted heteroaryl group having 2 to 30 carbon atoms for forming a ring.

4. The organic electroluminescence device of claim 1, wherein $Q_1$ is $NAr_1$, and $Ar_1$ is a substituted or unsubstituted phenyl group.

5. The organic electroluminescence device of claim 1, wherein Formula 1 is represented by Formulae 1-1 or 1-2:

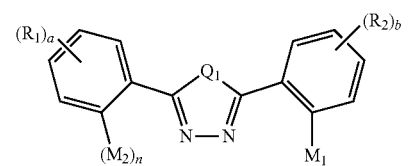

Formula 1-1

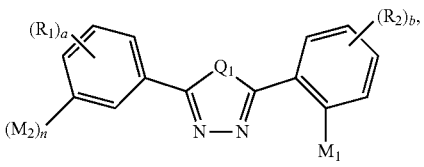

Formula 1-2 wherein in Formulae 1-1 and 1-2, $Q_1$, $R_1$, $R_2$, $M_1$, $M_2$, "n", "a" and "b" are the same as defined in Formula 1.

6. The organic electroluminescence device of claim 1, wherein "a" is 0.

7. The organic electroluminescence device of claim 1, wherein Formula 1 is represented by Formula 1-3:

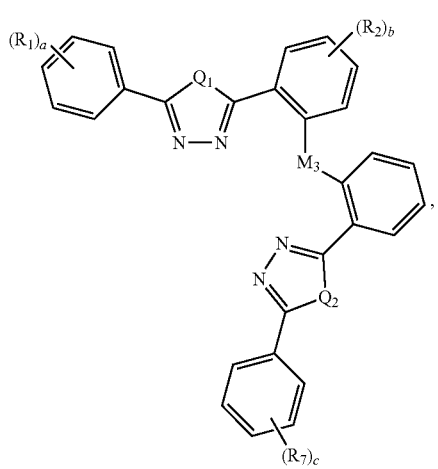

Formula 1-3 wherein in Formula 1-3, $Q_1$, $R_1$, $R_2$, "a" and "b" are the same as defined in Formula 1, definition of $Q_2$ is the same as the definition of $Q_1$, $Q_1$ and $Q_2$ are the same or different, $R_7$ is a hydrogen atom, a deuterium atom, a substituted or unsubstituted alkyl group having 1 to 10 carbon atoms, a substituted or unsubstituted aryl group having 6 to 30 carbon atoms for forming a ring, or a substituted or unsubstituted heteroaryl group having 2 to 30 carbon atoms for forming a ring, "c" is an integer of 0 to 5, and $M_3$ is represented by the following Formula 4:

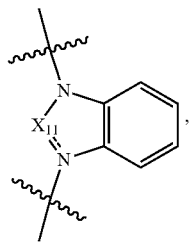

Formula 4 wherein in Formula 4, is $C=O$, or $CR_8$, and $R_8$ is a hydrogen atom, a deuterium atom, a substituted or unsubstituted alkyl group having 1 to 10 carbon atoms, a substituted or unsubstituted aryl group having 6 to 30 carbon atoms for forming a ring, or a substituted or unsubstituted heteroaryl group having 2 to 30 carbon atoms for forming a ring.

8. The organic electroluminescence device of claim 1, wherein

"b" is 0 or 1, if "b" is 1, $R_2$ is the same as $M_1$.

9. The organic electroluminescence device of claim 1, wherein the emission layer comprises a host and a dopant, and the host comprises the compound including nitrogen represented by Formula 1.

10. The organic electroluminescence device of claim 9, wherein the dopant is a phosphorescence dopant.

11. The organic electroluminescence device of claim 1, wherein the compound including nitrogen has the lowest triplet energy level of about 3.0 eV or more.

12. The organic electroluminescence device of claim 1, wherein the compound including nitrogen represented by Formula 1 is at least one selected from compounds represented in the following Compound Group 1:

Compound Group 1

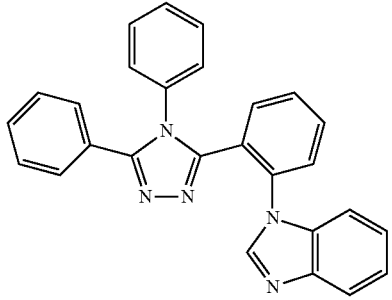

1

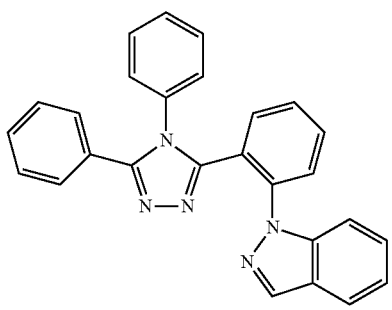

2

3
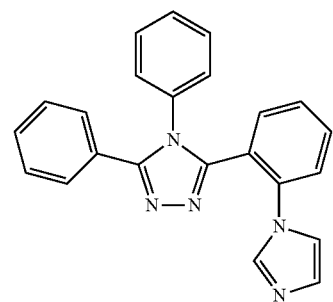
4
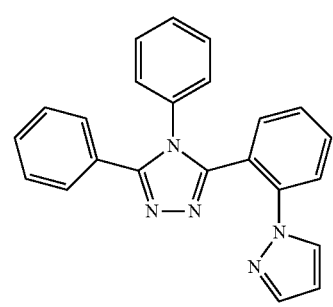
5
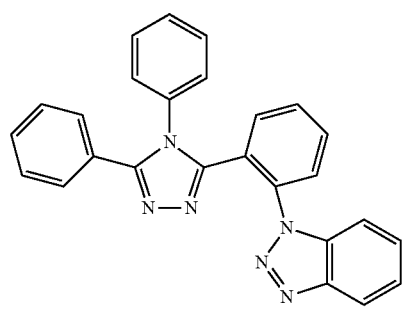
6
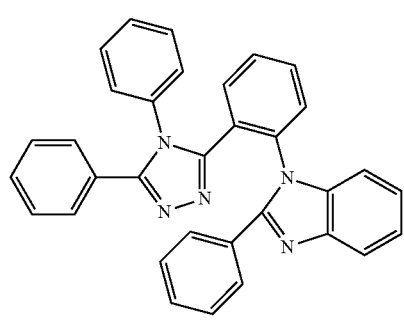
7
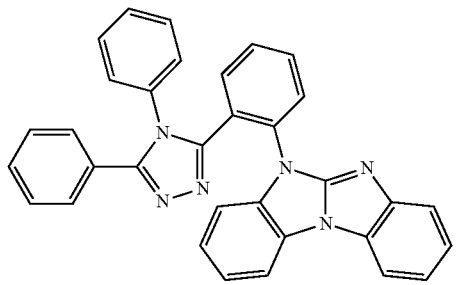
8
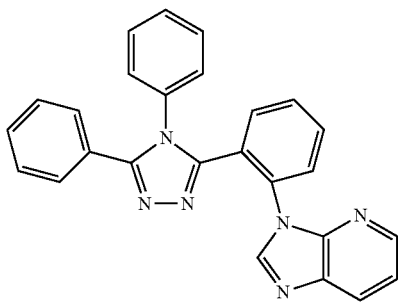
9
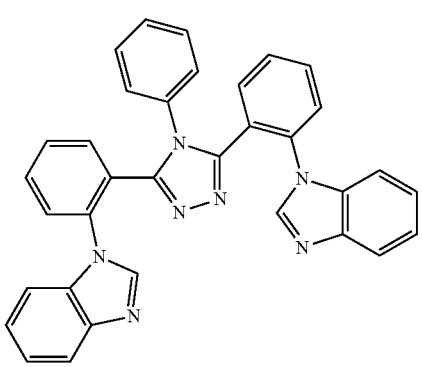
10
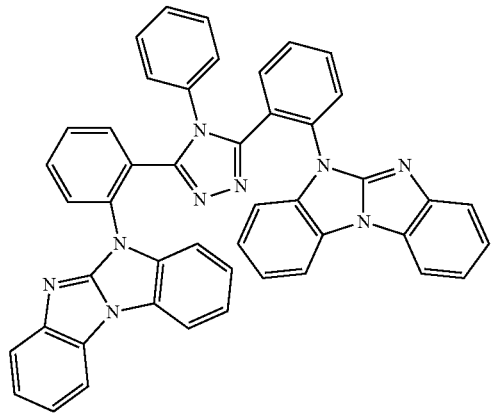
11
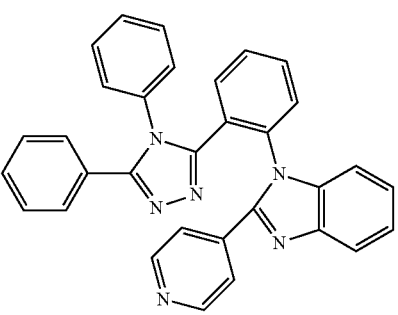

12
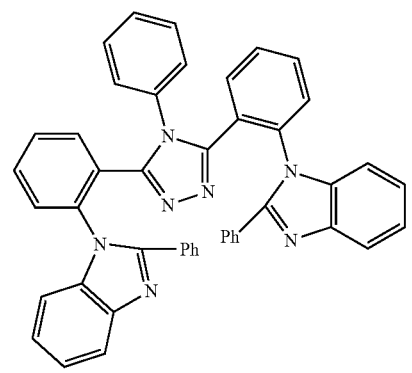
13
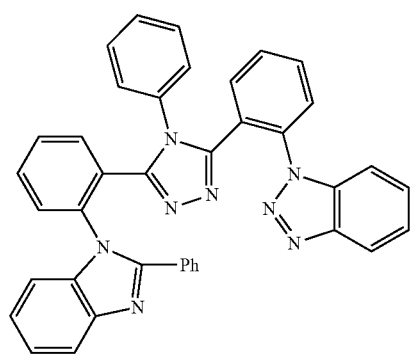
14
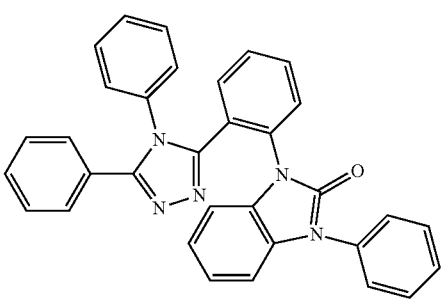
15
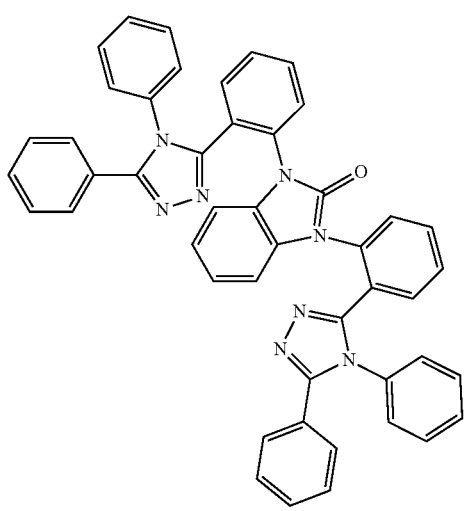
16
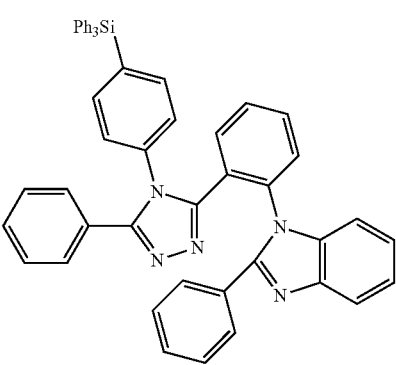
17
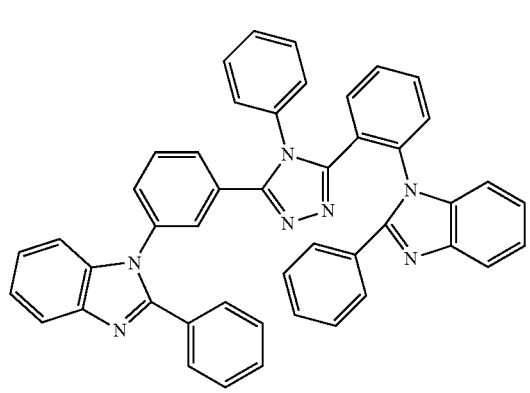
18
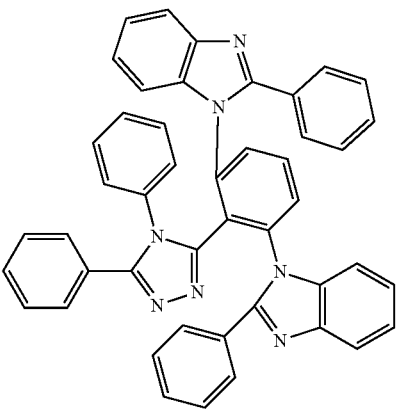
19
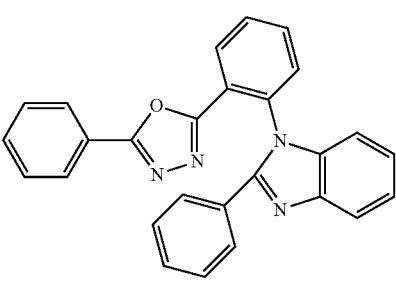

20
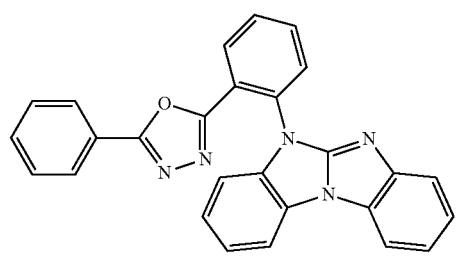
21
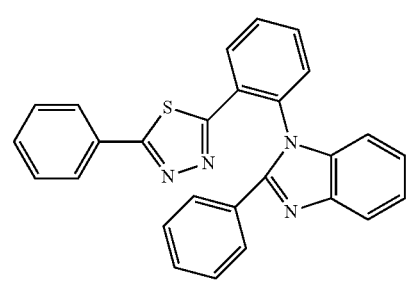
22
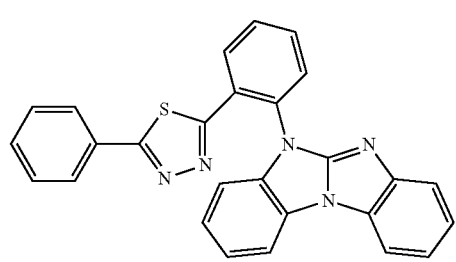
23
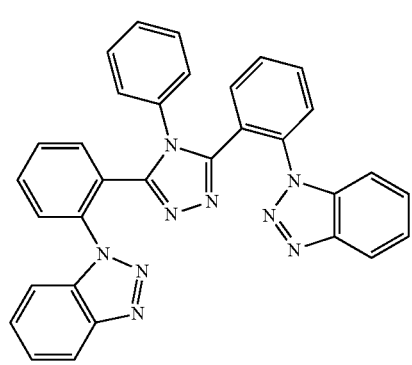
24
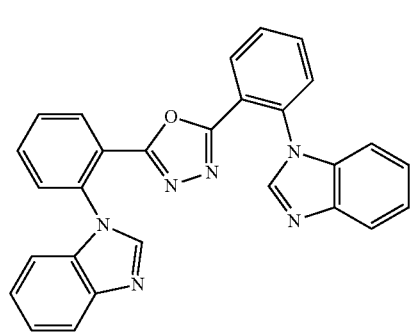
25
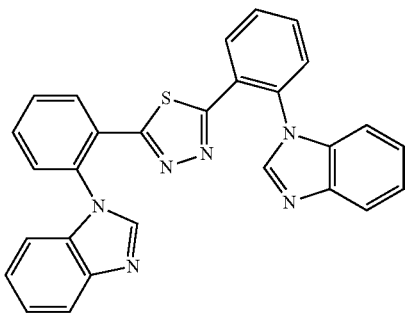
26
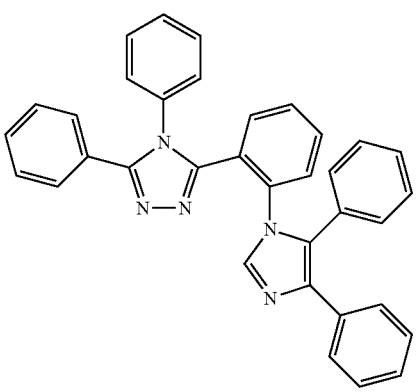
27
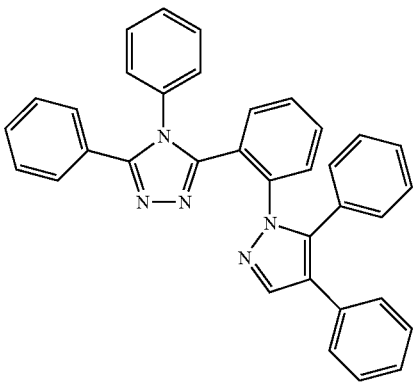
28
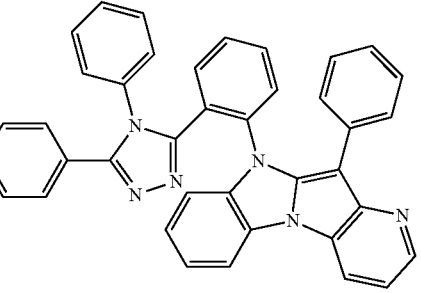

29
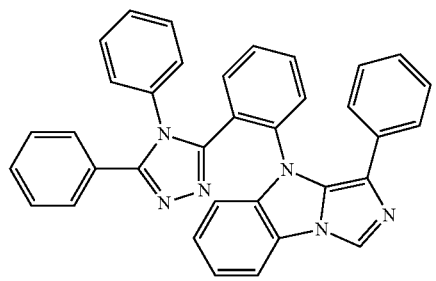
34
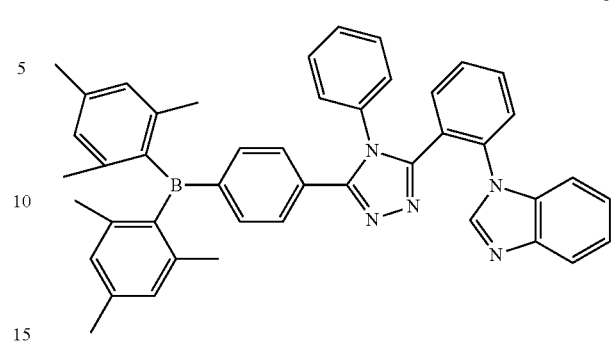
30
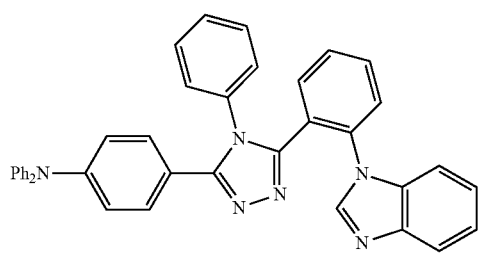
35
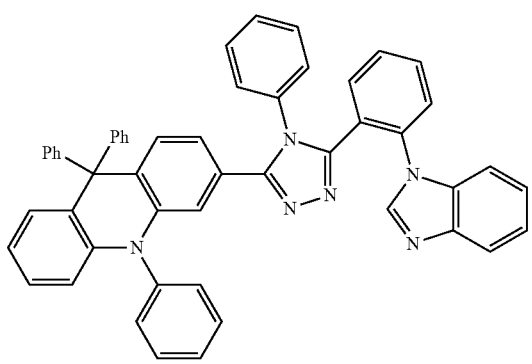
31
36
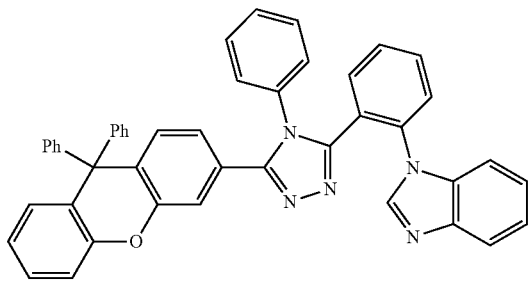
32
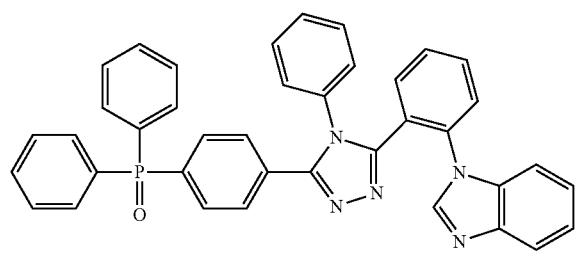
37
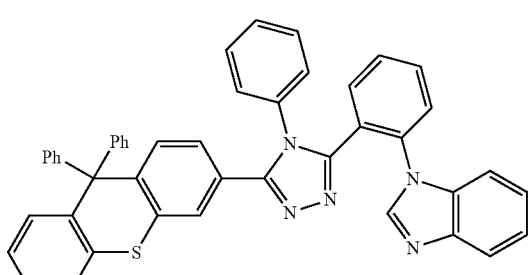
33
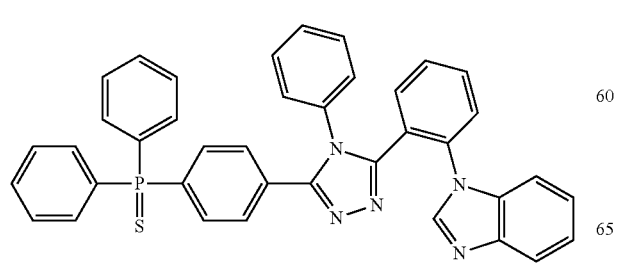
38
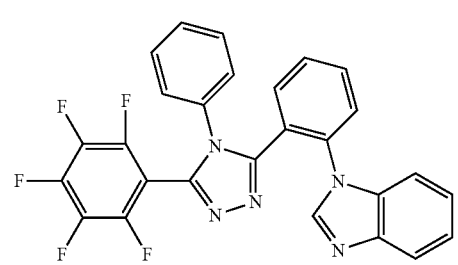

-continued

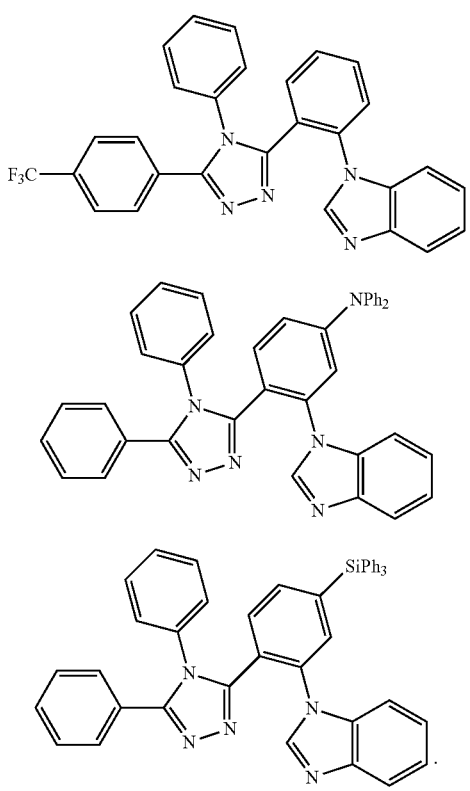

13. A compound including nitrogen represented by Formula 1:

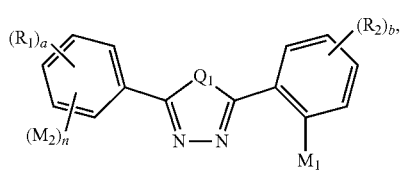

Formula 1 wherein in Formula 1,
Q₁ is NAr₁, O or S,
Ar₁ is a hydrogen atom, a deuterium atom, a substituted or unsubstituted aryl group having 6 to 30 carbon atoms for forming a ring, or a substituted or unsubstituted heteroaryl group having 2 to 30 carbon atoms for forming a ring,
R₁ and R₂ are each independently a hydrogen atom, a deuterium atom, a halogen atom, a substituted or unsubstituted amino group, a substituted or unsubstituted silyl group, a substituted or unsubstituted boryl group, a substituted or unsubstituted alkyl group having 1 to 10 carbon atoms, a substituted or unsubstituted aralkyl group having 6 to 30 carbon atoms, a substituted or unsubstituted haloalkyl group having 1 to 10 carbon atoms, a substituted or unsubstituted aryloxy group having 6 to 30 carbon atoms, a substituted or unsubstituted arylthio group having 6 to 30 carbon atoms, a substituted or unsubstituted phosphine oxy group, a substituted or unsubstituted phosphine sulfide group, a substituted or unsubstituted aryl group having 6 to 30 carbon atoms for forming a ring, or a substituted or unsubstituted heteroaryl group having 2 to 30 carbon atoms for forming a ring, and R₁ and R₂ are each independently optionally combined with an adjacent group to form a ring,
"a" and "b" are each independently an integer of 0 to 4,
"n" is 0 or 1, and
M₁ and M₂ are each independently represented by Formulae 2 or 3:

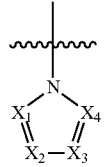

Formula 2

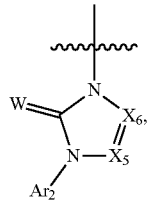

Formula 3 wherein in Formulae 2 and 3,
X₁ to X₆ are each independently CR₃ or N,
at least one of X₁ to X₄ is N,
R₃ is a hydrogen atom, a deuterium atom, a substituted or unsubstituted alkyl group having 1 to 10 carbon atoms, a substituted or unsubstituted aryl group having 6 to 30 carbon atoms for forming a ring, or a substituted or unsubstituted heteroaryl group having 2 to 30 carbon atoms for forming a ring, and R₃ is optionally combined with an adjacent group to form a ring,
W is O, NAr₃, or CAr₄Ar₅,
Ar₂ to Ar₅ are each independently a hydrogen atom, a deuterium atom, a substituted or unsubstituted alkyl group having 1 to 10 carbon atoms, a substituted or unsubstituted aralkyl group, a substituted or unsubstituted aryl group having 6 to 30 carbon atoms for forming a ring, or a substituted or unsubstituted heteroaryl group having 2 to 30 carbon atoms for forming a ring, and Ar₂ to Ar₅ are each independently optionally combined with an adjacent group to form a ring.

14. The compound including nitrogen of claim 13, wherein Formula 2 is represented by one of Formulae 2-1 to 2-3:

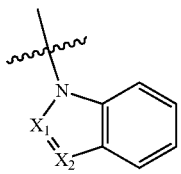

Formula 2-1

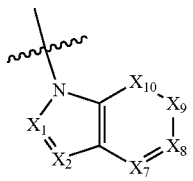

Formula 2-2

[Formula 2-3]

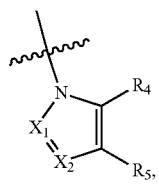

wherein in Formulae 2-1 to 2-3,
$X_1$ and $X_2$ are each independently $CR_3$ or N,
at least one of $X_1$ or $X_2$ is N,
$X_7$ to $X_{10}$ are each independently $CR_6$ or N,
at least one of $X_7$ to $X_{10}$ is N, and
$R_3$ to $R_6$ are each independently a hydrogen atom, a substituted or unsubstituted aryl group having 6 to 30 carbon atoms for forming a ring, or a substituted or unsubstituted heteroaryl group having 2 to 30 carbon atoms for forming a ring.

15. The compound including nitrogen of claim 13, wherein Formula 3 is represented by one of Formulae 3-1 to 3-4:

Formula 3-1

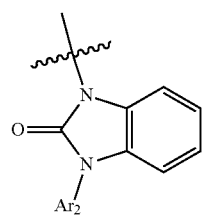

Formula 3-2

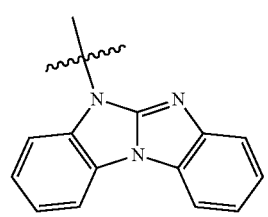

Formula 3-3

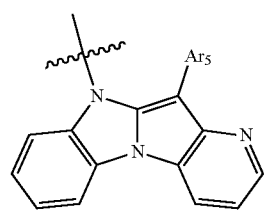

Formula 3-4

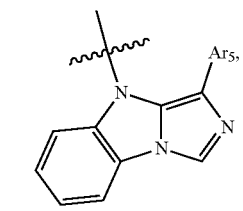

wherein in Formulae 3-1, 3-3 and 3-4,
$Ar_2$ and $Ar_5$ are each independently a substituted or unsubstituted aryl group having 6 to 30 carbon atoms for forming a ring, or a substituted or unsubstituted heteroaryl group having 2 to 30 carbon atoms for forming a ring.

16. The compound including nitrogen of claim 13, wherein $Q_1$ is $NAr_1$, and $Ar_1$ is a substituted or unsubstituted phenyl group.

17. The compound including nitrogen of claim 13, wherein Formula 1 is represented by Formula 1-1 or 1-2:

Formula 1-1

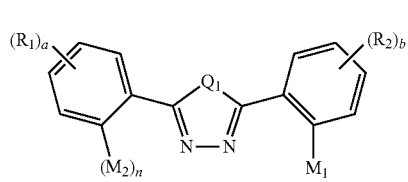

Formula 1-2

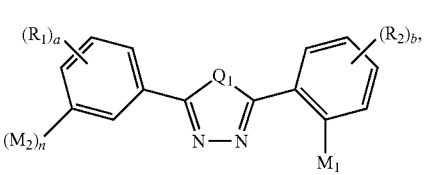

wherein in Formulae 1-1 and 1-2,
$Q_1$, $R_1$, $R_2$, $M_1$, $M_2$, "n", "a" and "b" are the same as defined in Formula 1.

18. The compound including nitrogen of claim 13, wherein "a" is 0.

19. The compound including nitrogen of claim 13, wherein Formula 1 is represented by Formula 1-3:

Formula 1-3

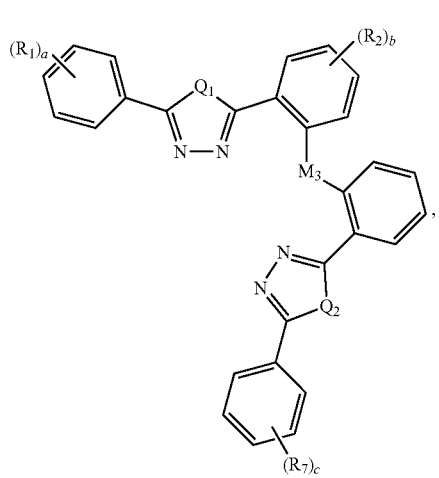

wherein in Formula 1-3,
$Q_1$, $R_1$, $R_2$, "a" and "b" are the same as defined in Formula 1,
definition of $Q_2$ is the same as the definition of $Q_1$,
$Q_1$ and $Q_2$ are the same or different,
$R_7$ is a hydrogen atom, a deuterium atom, a substituted or unsubstituted alkyl group having 1 to 10 carbon atoms, a substituted or unsubstituted aryl group having 6 to 30 carbon atoms for forming a ring, or a substituted or unsubstituted heteroaryl group having 2 to 30 carbon atoms for forming a ring,
"c" is an integer of 0 to 5, and $M_3$ is represented by Formula 4:

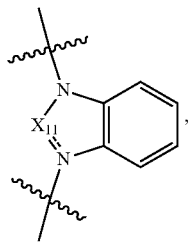

Formula 4 wherein in Formula 4, $X_{11}$ is C=O, or $CR_8$, and $R_8$ is a hydrogen atom, a deuterium atom, a substituted or unsubstituted alkyl group having 1 to 10 carbon atoms, a substituted or unsubstituted aryl group having 6 to 30 carbon atoms for forming a ring, or a substituted or unsubstituted heteroaryl group having 2 to 30 carbon atoms for forming a ring.

20. The compound including nitrogen of claim 13, wherein

"b" is 0 or 1, if "b" is 1, $R_2$ is the same as $M_1$.

21. The compound including nitrogen of claim 13, wherein the compound including nitrogen has the lowest triplet energy level of about 3.0 eV or more.

22. The compound including nitrogen of claim 13, wherein the compound including nitrogen represented by Formula 1 is at least one selected from compounds represented in the following Compound Group 1:

Compound Group 1

1

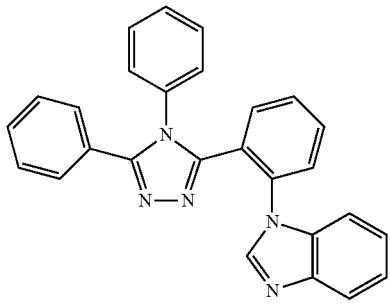

2

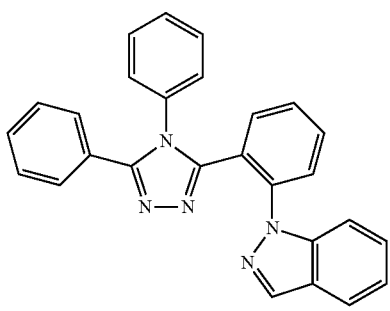

3

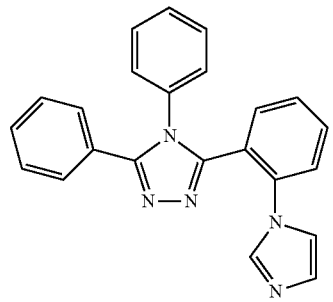

4

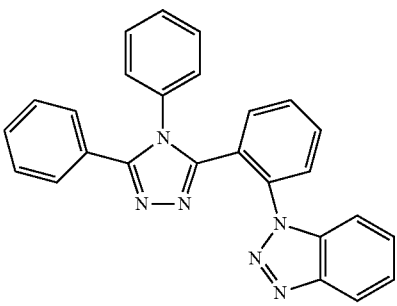

5

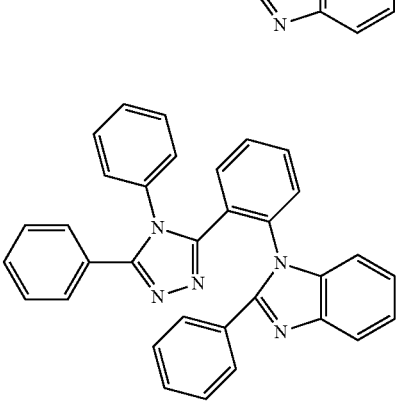

6

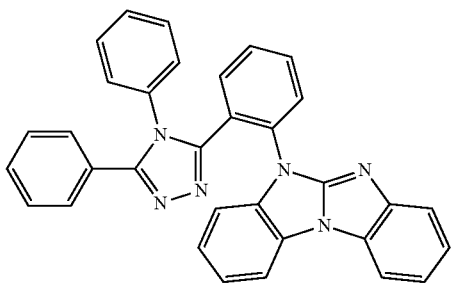

7

8
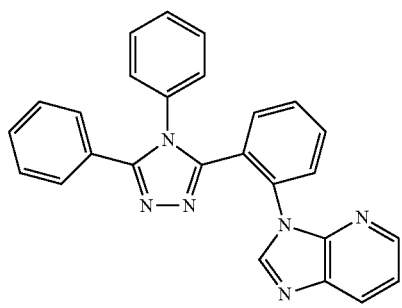
9
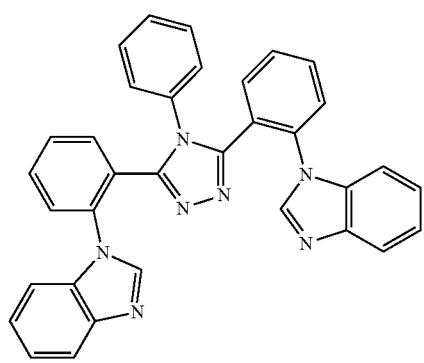
10
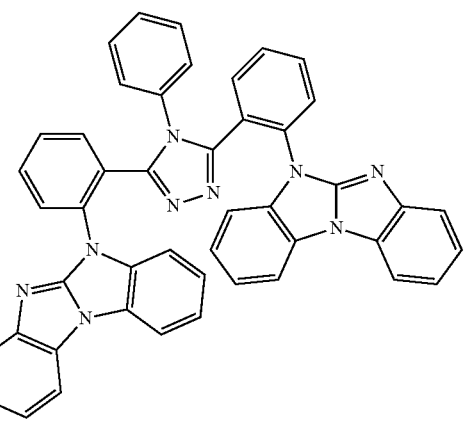
11
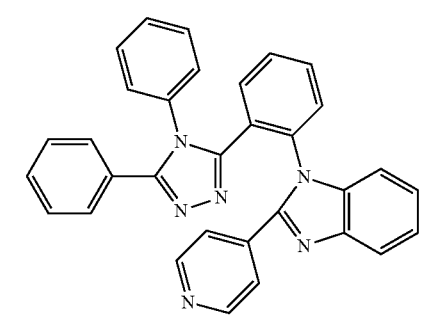
12
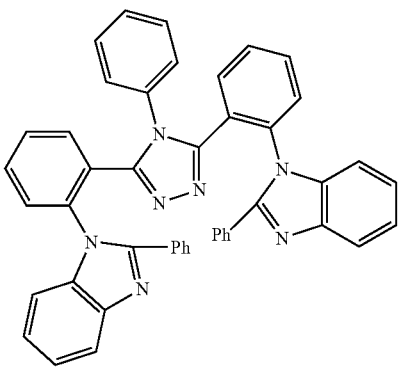
13
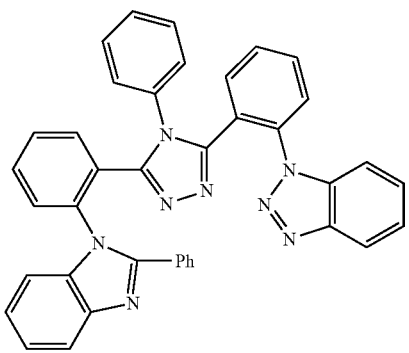
14
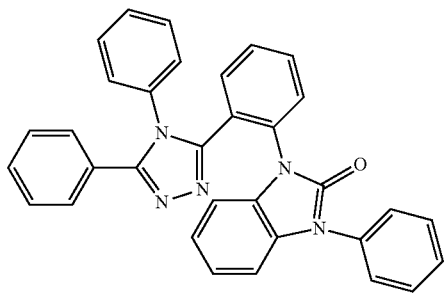
15
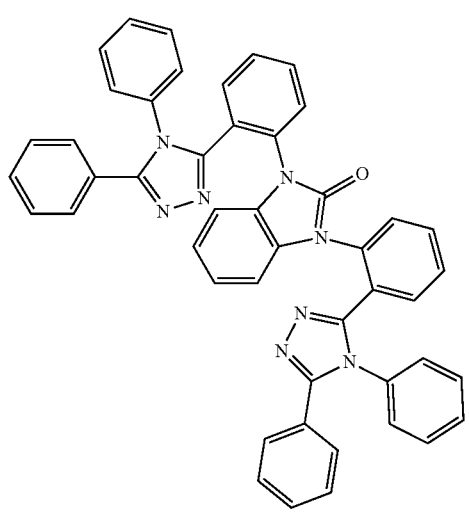

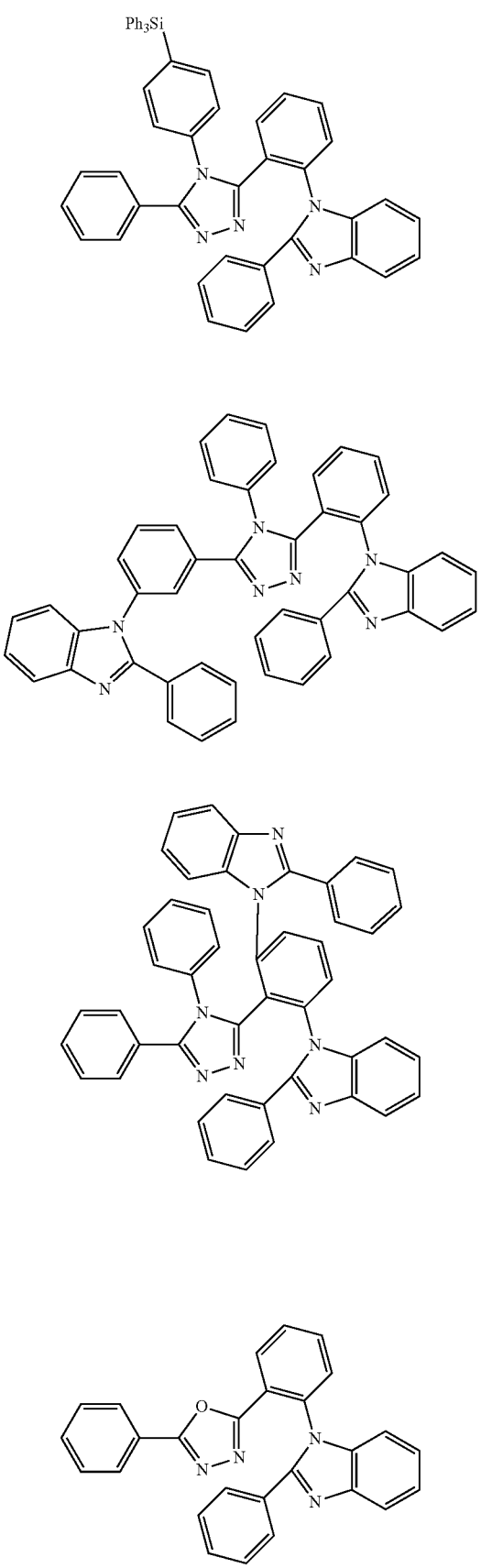
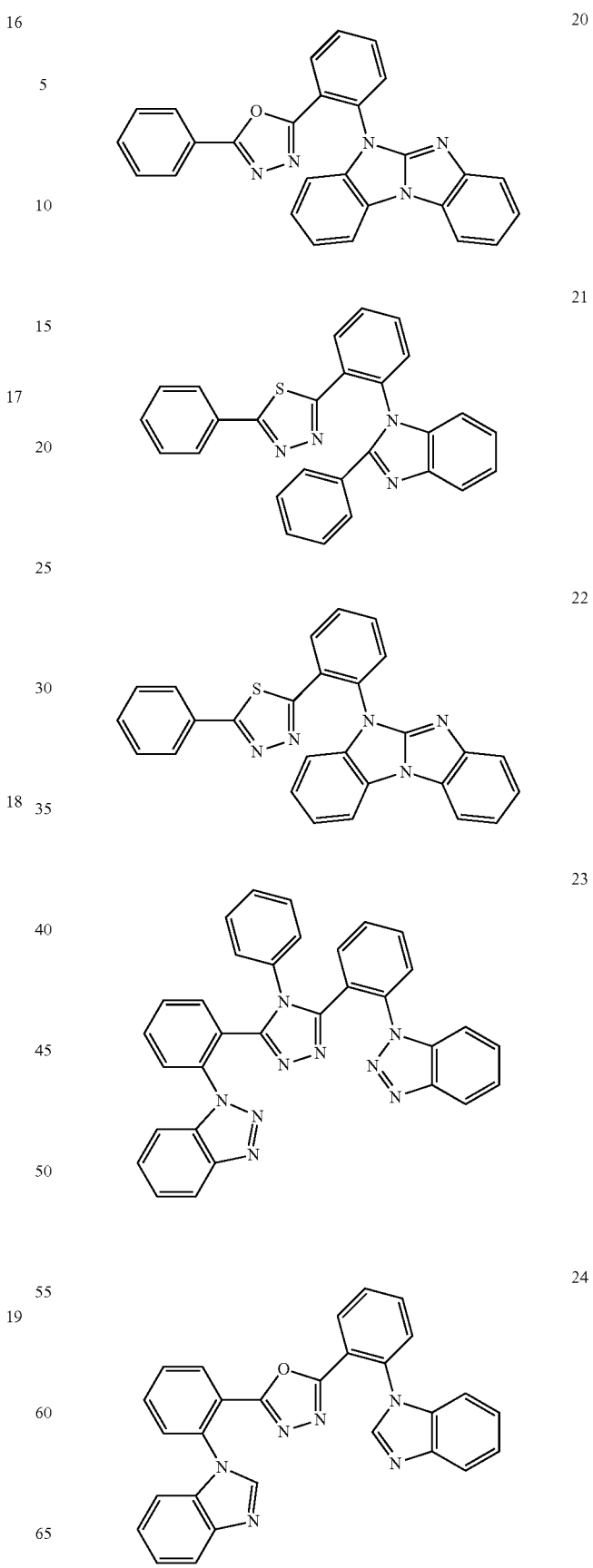

25
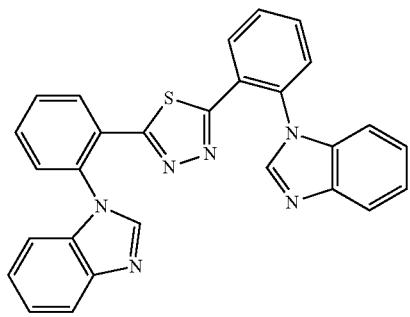
26
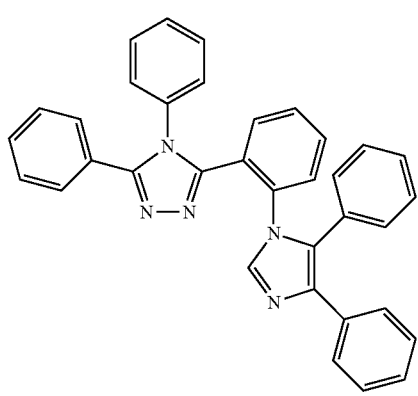
27
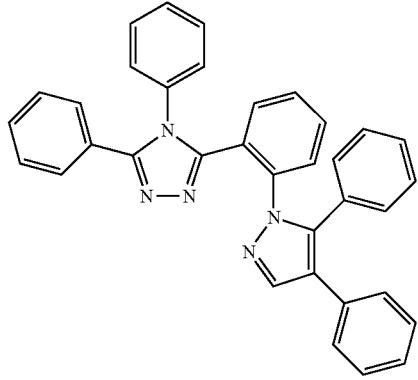
28
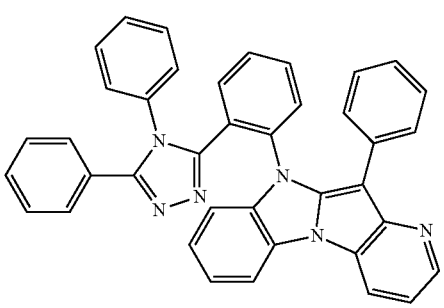
29
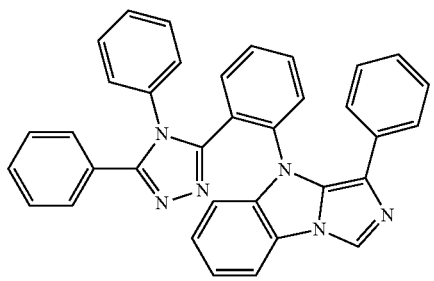
30
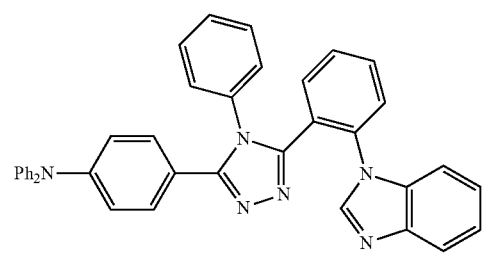
31
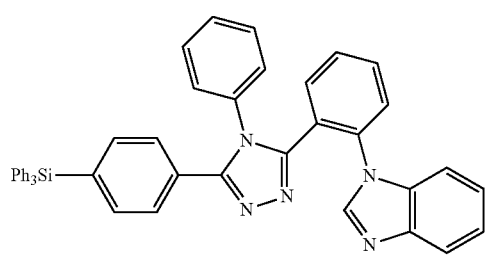
32
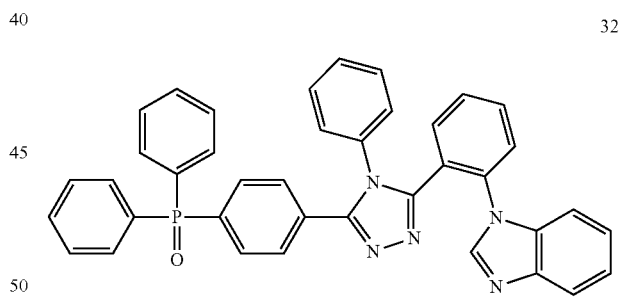
33
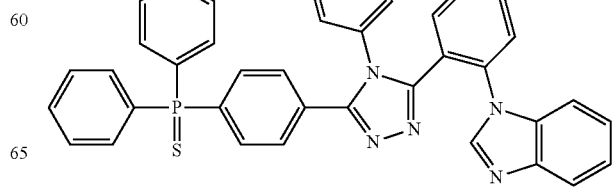

34
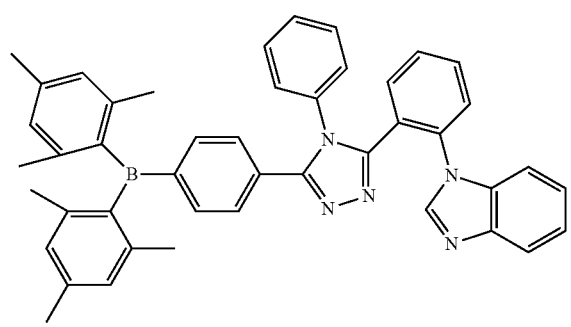
35
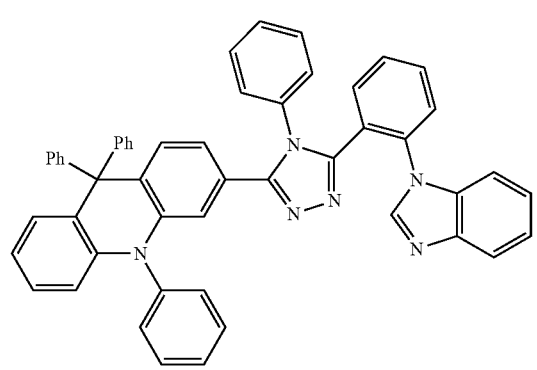
36
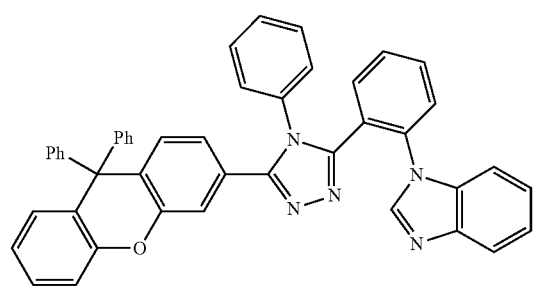
37
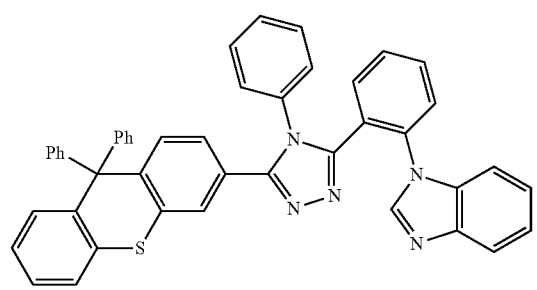
38
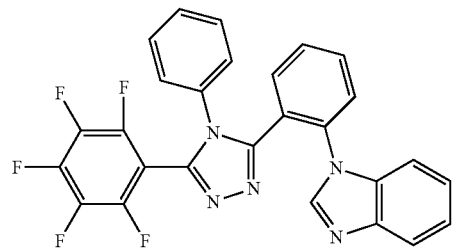
39
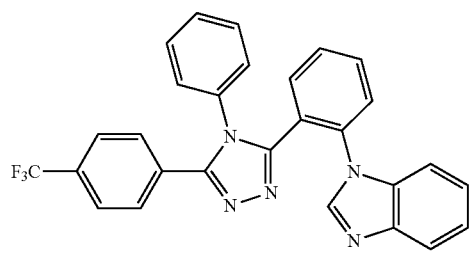
40
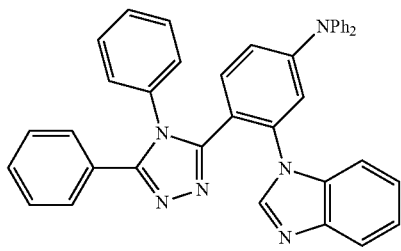
41
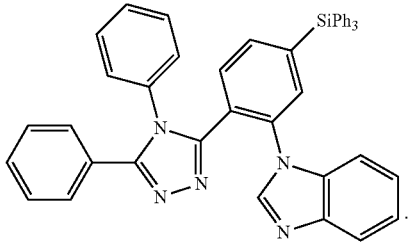
* * * * *

UNITED STATES PATENT AND TRADEMARK OFFICE
CERTIFICATE OF CORRECTION

PATENT NO. : 10,818,850 B2  
APPLICATION NO. : 16/129666  
DATED : October 27, 2020  
INVENTOR(S) : Akinori Yamatani Page 1 of 1

It is certified that error appears in the above-identified patent and that said Letters Patent is hereby corrected as shown below:

In the Claims  
    Column 42, Line 15, Claim 7    delete "is C=O" and insert -- $X_{11}$ is C=O --, therefor Signed and Sealed this  
Twenty-first Day of September, 2021

Drew Hirshfeld  
*Performing the Functions and Duties of the*  
*Under Secretary of Commerce for Intellectual Property and*  
*Director of the United States Patent and Trademark Office*